United States Patent
Cortés et al.

(10) Patent No.: US 7,231,238 B2
(45) Date of Patent: *Jun. 12, 2007

(54) HIGH TEMPERATURE SPIRAL SNAKE SUPERCONDUCTING RESONATOR HAVING WIDER RUNS WITH HIGHER CURRENT DENSITY

(75) Inventors: Balam Quitzé Andrés Willemsen Cortés, Ventura, CA (US); Albert H. Cardona, Santa Barbara, CA (US); Neal O. Fenzi, Santa Barbara, CA (US); Roger J. Forse, Santa Barbara, CA (US)

(73) Assignee: Superconductor Technologies, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/018,488

(22) Filed: Dec. 20, 2004

(65) Prior Publication Data

US 2005/0104683 A1 May 19, 2005

Related U.S. Application Data

(63) Continuation of application No. 10/167,938, filed on Jun. 10, 2002, now Pat. No. 6,895,262, which is a continuation of application No. 09/460,274, filed on Dec. 13, 1999, now Pat. No. 6,424,846, which is a continuation of application No. 08/885,473, filed on Jun. 30, 1997, now Pat. No. 6,026,311, which is a continuation-in-part of application No. 08/826,435, filed on Mar. 20, 1997, now abandoned, which is a continuation of application No. 08/297,289, filed on Aug. 26, 1994, now Pat. No. 5,616,539, which is a continuation-in-part of application No. 08/070,100, filed on May 28, 1993, now Pat. No. 5,618,777.

(51) Int. Cl.
*H01P 7/00* (2006.01)
*H01B 12/02* (2006.01)

(52) U.S. Cl. ............ 505/210; 505/700; 505/866; 333/99 S; 333/185; 333/219

(58) Field of Classification Search ......... 333/175, 333/185, 99 S, 219, 204; 336/200, 232; 505/210, 700, 705, 866

See application file for complete search history.

(56) References Cited

U.S. PATENT DOCUMENTS

| | | | |
|---|---|---|---|
| 2,411,555 A * | 11/1946 | Rogers | 333/202 |
| 3,925,740 A | 12/1975 | Steensma | |
| 4,075,591 A | 2/1978 | Haas | |
| 4,418,324 A | 11/1983 | Higgins | |
| 4,423,396 A | 12/1983 | Makimoto et al. | |
| 4,578,656 A | 3/1986 | Lacour et al. | |
| 4,642,591 A | 2/1987 | Kobayashi | |
| 4,701,727 A | 10/1987 | Wong | |
| 4,731,596 A | 3/1988 | Cruchon et al. | |
| 4,881,050 A | 11/1989 | Swanson, Jr. | |
| 4,981,838 A | 1/1991 | Whitehead | |
| 4,992,759 A | 2/1991 | Giradeau et al. | |
| 4,999,597 A | 3/1991 | Gaynor | |
| 5,023,578 A | 6/1991 | Kaneko et al. | |
| 5,038,105 A | 8/1991 | Codrington et al. | |
| 5,055,809 A | 10/1991 | Sagawa et al. | |
| 5,057,778 A | 10/1991 | Rath | |
| 5,066,933 A | 11/1991 | Komeda | |
| 5,078,621 A | 1/1992 | Nishikawa et al. | |
| 5,132,650 A | 7/1992 | Ikeda | |
| 5,136,268 A | 8/1992 | Fiedziuszko et al. | |
| 5,166,621 A | 11/1992 | Codrington et al. | |
| 5,172,084 A | 12/1992 | Fiedziuszko et al. | |
| 5,175,518 A | 12/1992 | Swanson, Jr. | |
| 5,208,213 A | 5/1993 | Ruby | |
| 5,210,494 A | 5/1993 | Brunner et al. | |
| 5,212,450 A | 5/1993 | Murphy-Boesch et al. | |
| 5,231,078 A | 7/1993 | Riebman et al. | |
| 5,258,626 A | 11/1993 | Suzuki et al. | |
| 5,291,146 A | 3/1994 | Friz | |
| 5,329,225 A | 7/1994 | Roshen et al. | |
| 5,336,112 A | 8/1994 | Michisita et al. | |
| 5,479,142 A | 12/1995 | Takahashi et al. | |
| 5,484,764 A | 1/1996 | Fiediusko et al. | |
| 5,521,568 A | 5/1996 | Wu et al. | |

| | | |
|---|---|---|
| 5,532,656 A | 7/1996 | Yoshimura |
| 5,616,538 A | 4/1997 | Hey-Shipton et al. |
| 5,616,539 A | 4/1997 | Hey-Shipton et al. |
| 5,618,777 A | 4/1997 | Hey-Shipton et al. |
| 5,638,037 A | 6/1997 | Kurisu et al. |
| 5,679,624 A | 10/1997 | Das |
| 5,699,025 A | 12/1997 | Kanoh et al. |
| 5,708,404 A | 1/1998 | Kurisu et al. |
| 5,719,539 A | 2/1998 | Ishizaki et al. |
| 5,721,195 A | 2/1998 | Grothe et al. |
| 5,780,404 A | 7/1998 | Bacon et al. |
| 5,786,303 A | 7/1998 | Mansour |
| 5,888,942 A | 3/1999 | Matthaei |
| 5,914,296 A | 6/1999 | Shen |
| 5,939,958 A | 8/1999 | Grounds, III et al. |
| 5,990,765 A | 11/1999 | Mansour et al. |
| 5,995,931 A | 11/1999 | Bahl et al. |
| 6,020,799 A | 2/2000 | Ishizaki et al. |
| 6,026,311 A * | 2/2000 | Willemsen Cortes et al. ............... 505/210 |
| 6,041,245 A | 3/2000 | Mansour |
| 6,057,271 A | 5/2000 | Kenjiro et al. |
| 6,075,427 A | 6/2000 | Tai et al. |
| 6,114,931 A | 9/2000 | Gevorgian et al. |
| 6,122,553 A | 9/2000 | Zhang et al. |
| 6,130,189 A | 10/2000 | Matthaei |
| 6,218,915 B1 | 4/2001 | Schallner |
| 6,222,429 B1 | 4/2001 | Satoh et al. |
| 6,239,674 B1 | 5/2001 | Enokihara et al. |
| 6,304,156 B1 | 10/2001 | Ishizaki et al. |
| 6,424,846 B1 | 7/2002 | Cortes et al. |
| 6,522,217 B1 | 2/2003 | Shen et al. |
| 6,633,208 B2 | 10/2003 | Salkola et al. |
| 6,700,459 B2 | 3/2004 | Raihn et al. |
| 6,895,262 B2 | 5/2005 | Cortés et al. |
| 2001/0025013 A1 | 9/2001 | Abdelmonem |
| 2001/0038320 A1 | 11/2001 | Abdelmonem |

FOREIGN PATENT DOCUMENTS

| | | |
|---|---|---|
| DE | 2629685 A1 | 1/1978 |
| EP | 0071508 A1 | 7/1982 |
| EP | 326498 A1 | 8/1989 |
| EP | 0337656 A2 | 10/1989 |
| EP | 357507 B2 | 3/1996 |
| JP | 60-19301 A2 | 1/1985 |
| JP | 60-033702 A | 2/1985 |
| JP | 60-220602 A | 11/1985 |
| JP | 62-207015 A | 9/1987 |
| JP | 62-254501 A | 11/1987 |
| JP | 63-204801 A2 | 8/1988 |
| JP | 01074705 A | 3/1989 |
| JP | 2-206201 A2 | 8/1990 |
| SU | 572865 T | 9/1977 |
| SU | 1224862 A1 | 4/1986 |
| SU | 1277256 A1 | 12/1986 |
| SU | 1309125 A1 | 5/1987 |
| SU | 1385165 A1 | 3/1988 |
| SU | 1709438 A1 | 1/1992 |

OTHER PUBLICATIONS

Cassinese, "High Power Handing Superconducting Planar Filters For Telecommunication Applications", International Journal Of Modern Physics B, 14, 25-27, 2000, 3092-3097.

Cristal, et al., "Hairpin-Line & Hybrid Hairpin-Line/Half-Wave Parallel Coupled Line Filters", IEEE Transactions On Microwave Theory & Techniques MTT-20, Nov. 1972, 719-728.

Hammond, "HTS And Cryogenics Technologies For Military Communications Systems", R&D Status Report, DABT63-97-C-0002, Sep. 1, 1996-Mar. 31, 1997.

Hejazi, "Compact Dual-Mode Filters for HTS Satellite Communication Systems", IEEE Microwave and Guided Wave Letters, 8, 8, Aug. 1998, 275-277.

Hey-Shipton Technical Hurdles For HTS Filters & Combiners For Cellular/PCM, STI Memo, Dec. 8, 1992.

Hey-Shipton, Ericsson Trip Report, STI Memo, Dec. 3, 1993.

Matthaei, et al., "High Temperature Superconducting 8.45 GHz Bandpass Filter For the Deep Space Network", 1993 IEEE Transactions On Microwave Theory and Techniques, MTT-5 International Symposium Digest, Jun. 14-18, 1993, Atlanta, Georgia, 1273-1276.

Matthaei, et al., "Novel, Staggered Resonator Array Superconducting 2.3 GHz Bandpass Filters", IEEE Transactions On Microwave Theory & Technique, 41, Dec. 1993, 2345-2352.

Matthaei, et al., "Novel Staggered Resonator Array Superconducting 2.3-GHz Bandpass Filter", 1993 MTT-S Int. Microwave Symp. Digest, paper LL-1.

Schmidt, et al., Measured Performance at 77 K Of Superconducting Microstrip Resonators & Filters, IEEE Transactions On Microwave & Theory & Technique, 39, 9, Sep. 1991, 1475-1479.

Superconductor Technologies, "LNA Development Plan For The PCS Cooled LNA/HTS Filter Product", Jul. 31, 1995.

Superconductor Technologies, "Technical Proposal", Apr. 18, 1996.

Hammond, et al., "Superconducting Tl-Ca-Ba-Cu-O Thin Film Microstrip Resonator and its Power Handling Performance At 77K", IEEE MTT-S Digest, 1990, 867-870.

Soares, et al., "Applications Of High-Temperature-Superconducting Filters and Cryo-Electronics For Satellite Communication", IEEE Transactions On Microwave Theory and Techniques, 48, 7, Jul. 2000, 1190-1198.

* cited by examiner

*Primary Examiner*—Benny Lee
(74) *Attorney, Agent, or Firm*—O'Melveny & Myers LLP

(57) ABSTRACT

Novel structures and methods for forming useful high temperature superconducting devices, most particularly resonators, are provided. Structures resulting in reduced peak current densities relative to known structures achieve numerous desirable benefits, especially including the reduced intermodulation effects of earlier resonators. In one aspect of this invention, a spiral in, spiral out resonator is provided, characterized in that it has an odd number of long runs, at least equal to five long runs, where the long runs are connected by turns, and wherein there are at least two sequential turns of the same handedness, followed by at least two turns of the opposite handedness. In yet another aspect of this invention, it has been discovered that reducing the size of the input and output pads of HTS resonators increases the relative inductance compared to the capacitance. Yet another resonator structure is a spiral snake resonator having a terminal end disposed within the resonator. A wide in the middle structure and wide at peak current density resonator structures utilize enlarged width portions of the resonator in those areas where current density is largest. In yet another aspect of this invention, operation of resonators in high modes, above the fundamental mode, reduce peak current densities. Resonators operated in modes in which current in adjacent long runs are in the same direction further serve to reduce current densities, and intermodulation effects. Symmetric current structures and modes of operation are particularly advantageous where far field effects are compensated for.

40 Claims, 16 Drawing Sheets

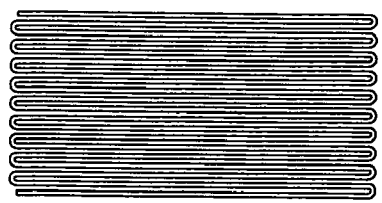
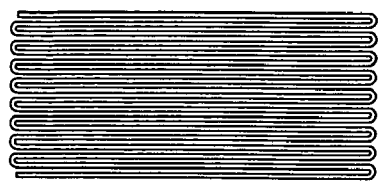
FIG. 17A  FIG. 17B
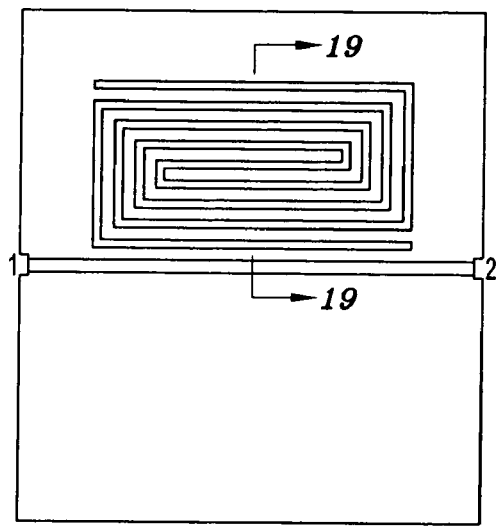
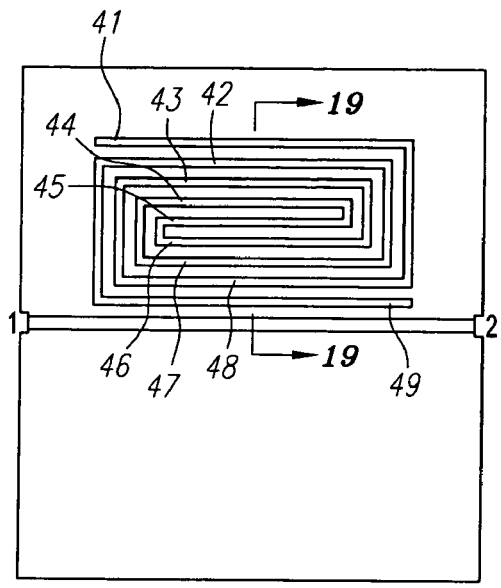
FIG. 18A  FIG. 18B
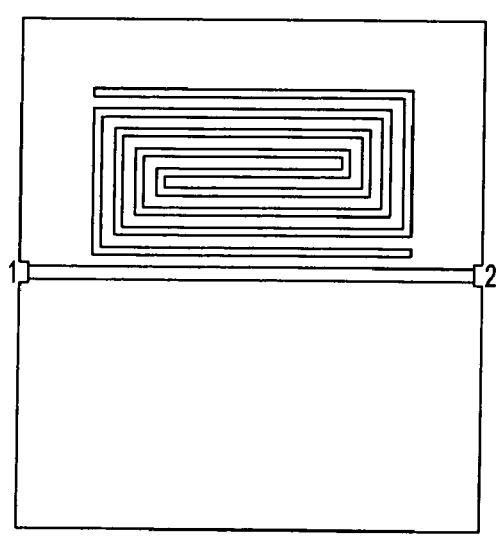
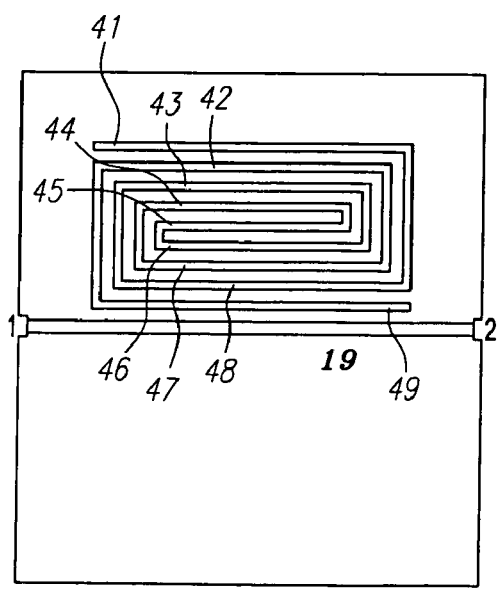
FIG. 18C  FIG. 18D

HIGH TEMPERATURE SPIRAL SNAKE SUPERCONDUCTING RESONATOR HAVING WIDER RUNS WITH HIGHER CURRENT DENSITY

RELATED APPLICATION

This application is a continuation of application Ser. No. 10/167,938, filed Jun. 10, 2002, now issued as U.S. Pat. No. 6,895,262 which is a continuation of application Ser. No. 09/460,274, filed Dec. 13, 1999, now issued as U.S. Pat. No. 6,424,846, which is a continuation of application Ser. No. 08/885,473, filed on Jun. 30, 1997, issued as U.S. Pat. No. 6,026,311, which is a continuation-in-part of application Ser. No. 08/826,435 (224/302), filed Mar. 20, 1997, now abandoned, which is a continuation of application Ser. No. 08/297,289, filed Aug. 26, 1994, entitled "Lumped Element Filters", issued as U.S. Pat. No. 5,616,539, which is in turn a continuation-in-part of application Ser. No. 08/070,100 filed May 28, 1993, entitled "Lumped High Temperature Superconductor Lumped Elements and Circuits Therefrom" (as amended), issued as U.S. Pat. No. 5,618,777 on Apr. 8, 1997.

FIELD OF THE INVENTION

This invention relates to structures and methods formed from high temperature superconductors. More particularly, it relates to devices such as resonators having high Q and reduced intermodulation distortion for use as passive microwave devices.

BACKGROUND OF THE INVENTION

Electrical components come in various conventional forms, such as inductors, capacitors and resistors. A lumped electrical element is one whose physical size is substantially less than the wave length of the electromagnetic field passing through the element. A distributed element is one whose size is larger than that for a lumped element. As an example, a lumped element in the form of an inductor would have a physical size which is a relatively small fraction of the wave length used with the circuit, typically less than ⅛ of the wavelength.

Inductors, capacitors and resistors have been grouped together into useful circuits. Useful circuits including those elements include resonant circuits and filters. One particular application has been the formation of filters useful in the microwave range, such as above 500 MHZ.

Considering the case of conventional microwave filters, there have been basically three types. First, lumped element filters have used separately fabricated air wound inductors and parallel plate capacitors, wired together into a filter circuit. These conventional components are relatively small compared to the wave length, and accordingly, make for a fairly compact filters. However, the use of separate elements has proved to be difficult in manufacture, and resulting in large circuit to circuit differences. The second conventional filter structure utilizes mechanical distributed element components. Coupled bars or rods are used to form transmission line networks which are arranged as a filter circuit. Ordinarily, the length of the bars or rods is ¼ or ½ of the wave length at the center frequency of the filter. Accordingly, the bars or rods can become quite sizeable, often being several inches long, resulting in filters over a foot in length. Third, printed distributed element filters have been used. Generally they comprise a single layer of metal traces printed on an insulating substrate, with a ground plane on the back of the substrate. The traces are arranged as transmission line networks to make a filter. Again, the size of these filters can become quite large. The structures also suffer from various responses at multiples of the center frequency.

Various thin-filmed lumped element structures have been proposed. Swanson U.S. Pat. No. 4,881,050, issued Nov. 14, 1989, discloses a thin-film microwave filter utilizing lumped elements. In particular, a capacitor π network utilizing spiral inductors and capacitors is disclosed. Generally, a multi-layer structure is utilized, a dielectric substrate having a ground plane on one side of the substrate and multiple thin-filmed metal layers and insulators on the other side. Filters are formed by configuring the metal and insulation layers to form capacitive π-networks and spiral inductors. Swanson U.S. Pat. No. 5,175,518 entitled "Wide Percentage Band With Microwave Filter Network and Method of Manufacturing Same" discloses a lumped element thin-film based structure. Specifically, an alumina substrate has a ground plane on one side and multiple layer plate-like structures on the other side. A silicon nitride dielectric layer is deposited over the first plate on the substrate, and a second and third capacitor plates are deposited on the dielectric over the first plate.

Historically, such lumped element circuits were fabricated using normal, that is, non-superconducting materials. These materials have an inherent loss, and as a result, the circuits have various degree of lossiness. For resonant circuits, the loss is particularly critical. The quality factor Q of a device is a measure of its power dissipation or lossiness. Resonant circuits fabricated from normal metals have Q's at best on the order of a few hundred.

With the discovery of high temperature superconductivity in 1986, attempts have been made to fabricate electrical devices from these materials. The microwave properties of the high temperature superconductors has improved substantially since their discovery. Epitaxial superconductive thin films are now routinely formed and commercially available. See, e.g., R. B. Hammond, et al., "Epitaxial $Tl_2Ca_1Ba_2Cu_2O_8$ Thin Films With Low 9.6 GHz Surface Resistance at High Power and Above 77 K", Appl. Phy. Lett., Vol. 57, pp. 825–827, 1990. Various filter structures and resonators have been formed. Other discrete circuits for filters in the microwave region have been described. See, e.g., S. H. Talisa, et al., "Low- and High-Temperature Superconducting Microwave Filters," IEEE Transactions on Microwave Theory and Techniques, Vol. 39, No. 9, September 1991, pp. 1448–1554.

The need for compact, reliable narrow band filters has never been stronger. Applications in the telecommunication fields are of particular importance. As more users desire to use the microwave band, the use of narrow band filters will increase the number of users in the spectrum. The area from 800 to 2,000 MHZ is of particular interest. In the United States, the 800 to 900 MHz range is used for analog cellular communications. The personal communications services are planned for the 1,800 to 2,000 MHZ range.

Many passive microwave devices, for example, resonators, filters, antennas, delay lines and inductors, have been fabricated in planar form utilizing high temperature superconducting thin films. As described, such structures are often smaller than conventional technologies in terms of physical size. However, these devices are also limited in their size given the constraints of fabricating high quality, epitaxial films. As a result, devices fabricated in HTS films are often of a quasi-lumped element nature, that is, where the nominal size the device is smaller than the wavelength of operation. This often results in folding of devices, which leads to significant coupling between lines.

Despite the clear desirability of improved electrical circuits, including the known desirability of converting circuitry to include superconducting elements, efforts to date have been less than satisfactory in all regards. It has proved to be especially difficult in substituting high temperature superconducting materials to form circuits without severely degrading the intrinsic Q of the superconducting film. These problems include circuit structure, radiative loss and tuning and have remained in spite of the clear desirability of an improved circuit.

SUMMARY OF THE INVENTION

This patent relates to various novel structures and methods for forming high temperature superconducting devices, most particularly resonators. These devices have high Q, that is, at least in excess of 1,000, more preferably in excess of 25,000, and most preferably in excess of 50,000. Generally, these inventive structures reduce peak current densities relative to known structures. One significant result of reduced current density is in reduced intermodulation effects. In one embodiment, a snake resonator includes a plurality of long runs, connected by a plurality of turns, wherein certain ones of the long runs are wider than certain other ones of the long runs the wider runs being those that would have a higher current density if all runs were of equal width.

In one aspect of this invention, a spiral snake resonator having a terminal end disposed within the resonator is provided. In the preferred mode of this embodiment, multiple long runs are connected by turns, where the turns at one end of the resonator are concentric semicircles, with the center of radius being disposed between long runs. The turns at the second ends of the resonator are also concentric semicircles, though with the center of curvature being disposed at the end of a centrally disposed long run.

In one specific preferred embodiment, a spiral snake resonator includes a plurality of N long runs, each one of the plurality of N long runs having two ends and a plurality of turns connecting the plurality of N long runs to each other in a spiral snake configuration. The resonator is characterized in that one end of a first long run of the plurality of N long runs is connected to one end of a second long run of the plurality of N long runs by a first turn of the plurality of turns of a first handedness, and the other end of the second long run is connected to one end of a third long run of the plurality of N long runs by a second turn of the plurality of turns of said first handedness, the third long run being disposed between the first long run and the second long run, the remaining long runs of the plurality of N long runs being by repeating the connections of the first, second and third long run for the remaining plurality of N long runs using the remaining plurality of turns starting at the other end of the third long run and terminating at one end of the Nth long run of the plurality of N long runs. The resonator is further characterized by the feature that the plurality of turns located at the first ends of the plurality of long runs are concentric with each other around a center point disposed between long runs N and N–1 and wherein the plurality of turns located at the second ends of the plurality of long runs are concentric with each other around a center point disposed on the end of the Nth long run.

Accordingly, it is an object of this invention to provide improved high temperature superconducting structures.

It is yet a further object of this invention to provide improved resonators having reduced intermodulation.

It is yet a further object of this invention to provide resonators having reduced peak current densities.

It is yet a further object of this invention to provide high Q, superconducting resonators having reduced intermodulation effects.

BRIEF DESCRIPTION OF THE DRAWINGS

FIG. 17a is a plan view of a zig-zag or serpentine resonator at its first harmonic and FIG. 17b is a plan view of a wide at peaks resonator at its first harmonic.

FIGS. 18a, 18b, 18c and 18d show outputs of electromagnetic model simulations for the magnitude in the fundamental mode (FIG. 18a), the phase in the fundamental mode (FIG. 18b), the magnitude in the first harmonic mode (sometimes referred to as "ALF") (FIG. 18c) and the phase in that mode (FIG. 18d).

DETAILED DESCRIPTION OF THE INVENTION

Figure 1:
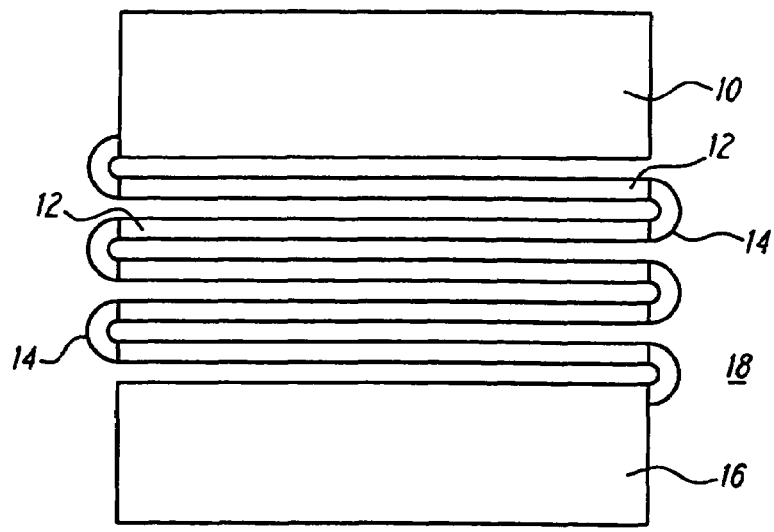
FIG. 1 is a plan view of a quasi-lumped element resonator having wide input and output pads in a serpentine or zig-zag inductor structure.

FIG. 1 shows a plan view of a quasi-lumped element resonator (QLE) having enlarged input and output pads. An input pad 10 (the designation of input and output being arbitrary, and reversible) and an output pad 16 are disposed on opposite sides of a serpentine or zig-zag resonator region 18. Generally parallel long runs 12 are disposed substantially parallel to the longer edge of the input pad 10 and output pad 16. A first long run 12 adjacent to the input pad 10 is connected to a first turn 14 which electrically couples the input pad 10 to the first long run 12. Adjacent long runs 12 are then coupled to their nearest neighbor long runs 12 by corresponding turns 14.

The input pads 10 and output pad 16 serve to increase the equivalent capacitance to ground relative to a structure having no or smaller input and output pads. Preferably, the amount of equivalent capacitance to ground is selected in accordance with the electrical requirements of the circuit. As shown in FIG. 1, the total area occupied by the input pad 10 and output pad 16 exceeds that area occupied by the zig-zag resonator region 18.

The center frequency $f_c$ of such a resonator is $$f_c \propto 1/\sqrt{LC}$$

wherein L is the inductance and C is the capacitance of the resonator. A condition of resonance is that the energy stored in the magnetic field $W_1$ and the energy stored in the electric field $W_c$ must be equal to:

$$W = W_c = W_l = \frac{1}{2}CV^2 = \frac{1}{2}LI^2$$

wherein V is the voltage and I is the current, and W is the energy stored at resonance.

When the unloaded Q is much larger than the loaded Q, as is often the case for superconducting filters, then the stored energy at resonance, W, is determined by the loaded Q. Thus, if the frequency and loaded Q are fixed, it is clear that in order to decrease the circulating current we must increase L, while simultaneously decreasing C to preserve the resonant frequency.

Figure 2:
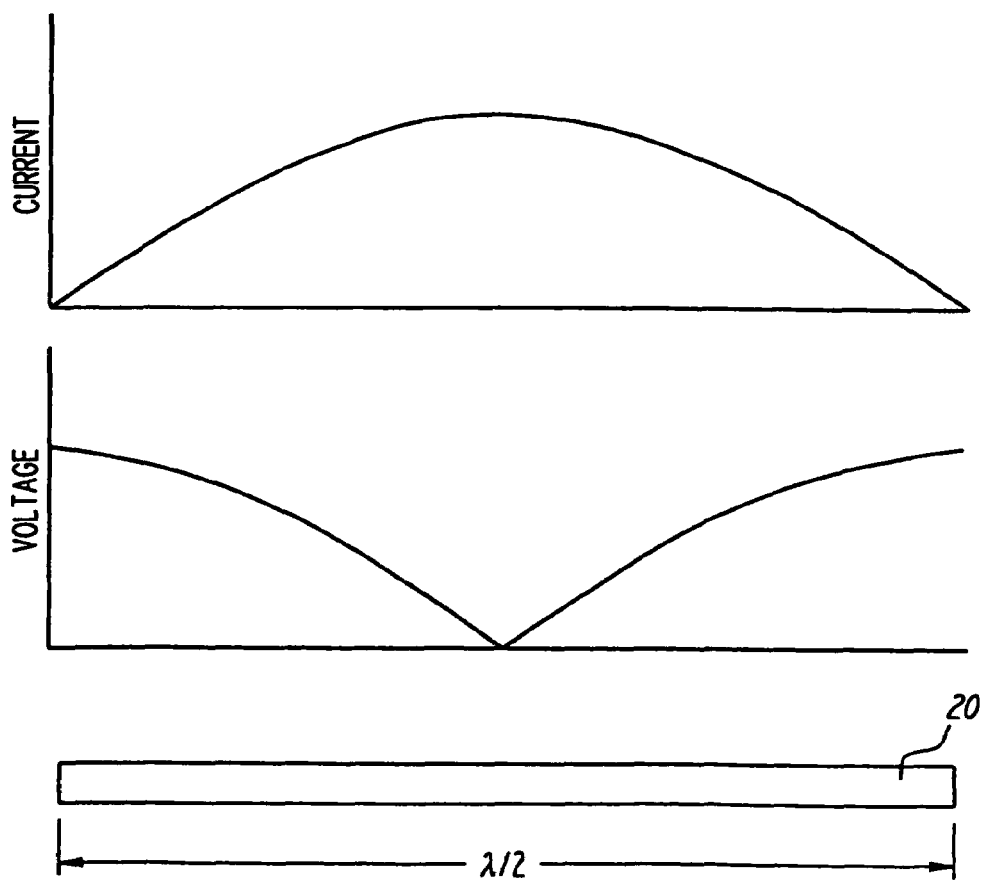
FIG. 2 is a plot of the current and voltage distributions of a ½ wavelength resonator at its fundamental resonance frequency, plotted above a ½ wavelength resonator structure.

FIG. 2 shows the current and voltage distributions of a ½ wavelength (λ/2) resonator at its fundamental resonance frequency. A microstrip format may be utilized to implement a ½ wavelength transmission line. Such structures generally have inductance and capacitance which form the resonator distributed along the line 20. The current distribution in such a structure at resonance is of the form $\sin(\pi x/l)$ having a maximum in the center of the resonator. The voltage distribution is of the form $\cos(\pi x/l)$ with maxima at the ends of the resonator.

Figure 3:
FIG. 3 is a plan view of a zig-zag snake resonator having no significant input and output pad structures.

FIG. 3 shows a plan view of a zig-zag or serpentine snake resonator 30. A first long run 31 is connected to a nearest neighbor long run 32 by a turn 36. In similar fashion, the third long run 33 is connected to the nearest neighbor long run 32 by turn 37. This pattern is repeated until reaching a last long run 39.

FIG. 3 differs from FIG. 1 principally in that the input pad 10 and output pad 16 of FIG. 1 are eliminated or significantly reduced in size. By reducing the size of the capacitor pads 10, 16, the effective inductance of the quasi-lumped resonator is increased in FIG. 3 relative to FIG. 1. For a fixed frequency and loaded Q, this implies that the current density in the resonator can significantly be reduced by removal of the large capacitor pads. This has the effect of making the resonators behave more like folded distributed (½ wavelength) resonators. As an added current density reducing benefit, the linewidth of these resonators is usually higher than the linewidth at the highest current point in their QLE counterparts.

To a first approximation, the unloaded Q of an HTS resonator is $Q=wL/R_s$ where w is the resonant frequency and $R_s$ is the surface resistance at that frequency. Thus, we see an additional advantage of these resonators over their QLE counterparts in terms of their higher unloaded Qs.

Using these structures, small area resonators can reliably be constructed which have the following desirable properties.

| Resonator Area | Resonant Frequency | Unloaded Q | Loaded Q | IMD (Input Power: −20 dBm) |
| --- | --- | --- | --- | --- |
| <1 cm² | 850 MHZ | >50,000 | ~1000 | <−80 dBc |

Figure 4:
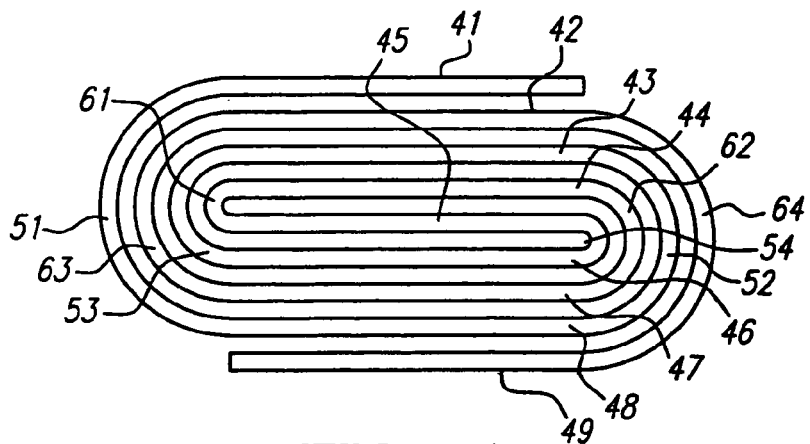
FIG. 4 is a plan view of a spiral in, spiral out structure having no significant input and output pad structures.

FIG. 4 shows a plan view of a spiral in, spiral out snake resonator. A first long run 41 is connected to a second long run 48 by a first turn 51. The first turn 51 has a preselected handedness, here taken to be left-handed, though the designation of left and right-handed is arbitrary and therefore reversible. The second long run 48 is then connected by second turn 52, which is of the same handedness as is the first turn 51. The second turn 52 is connected to the third long run 43, which is then connected to turn 53 which is again of the same handedness of first turn 51 and second turn 52. The third turn 52 is connected to fourth long run 46, which is then connected to fourth turn 54, which is again of the same handedness of the preseating turns 51, 52 and 53. A fifth long run 45 is connected to the fourth turn 54. The fifth long run 45, being the center long run, namely, the line of symmetry for the resonator, then connects to a first turn of opposite handedness 61 which in turn connects to a sixth long run 44. The run 44 connects to a second turn of opposite handedness 62, which has the same handedness as the first turn of opposite handedness 61, which is opposite to the handedness of the first turn 51. The second turn of opposite handedness 62 connects to the seventh long run 47, which connects to the third turn of opposite handedness 63 which connects to the seventh long run 42, which connects to the fourth turn of opposite handedness 64 which connects to the ninth or last long run 49.

The spiral in, spiral out structure of FIG. 4 may be implemented with varying number of long runs and turns. Generally, the following criteria describe the topology of the spiral in, spiral out structure. The spiral in, spiral out structure includes an odd number of long runs, identified to be N, where N is $\geq 5$. Numbering the long runs sequentially from 1 to N, the first long run is connected to the N-first long run by a turn of a first handedness. Long run N−1 is connected to long run 3 by a second turn of first handedness. This sequence is repeated until a turn of the first handedness connects to long run (N+1)/2. Long run (N+1)/2 is connected to long run (N+3)/2 by a turn of opposite handedness. Long run (N+3)/2 is connected by a second turn of opposite handedness to a long run (N−3)/2. This process is repeated until the last long run (N) is reached.

Figure 5:
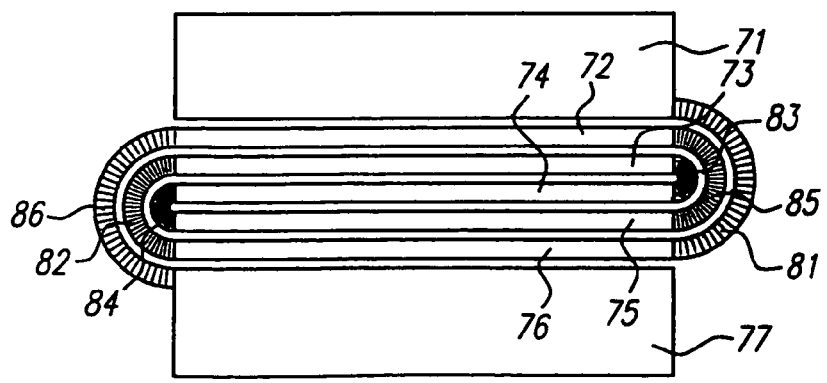
FIG. 5 is a plan view of a spiral in, spiral out structure with input and output pads.

FIG. 5 shows a plan view of a lumped element spiral in, spiral out resonator having enlarged input and output pads. In comparison to FIG. 4 where nine long runs 40, 41 . . . 49 are utilized, FIG. 5 has seven long runs 71, 72, 73, 74, 75, 76, 77. The first long run 71 has an enlarged width relative to other runs, serving to have increased capacitance. The first long run 71 is connected to first turn of first handedness 81 to the sixth long run 76. The long run 76 is connected by the second turn of first handedness 82 to the third long run 73, which is in turn connected by the third turn of first handedness 83 to the center long run 74. The center long run 74 is connected in turn to first turn of opposite handedness 84, which is connected to the fifth long run 75, which is connected to second turn of second handedness 85 to the second long run 72, which is in turn connected to the third turn of second handedness 86 to the last long run or output capacitor pad 77. The output capacitor pad 77 has a width which is enlarged relative to the other interior long runs, and is shown having the same width as the first input capacitor pad or long run 71.

Figure 6:
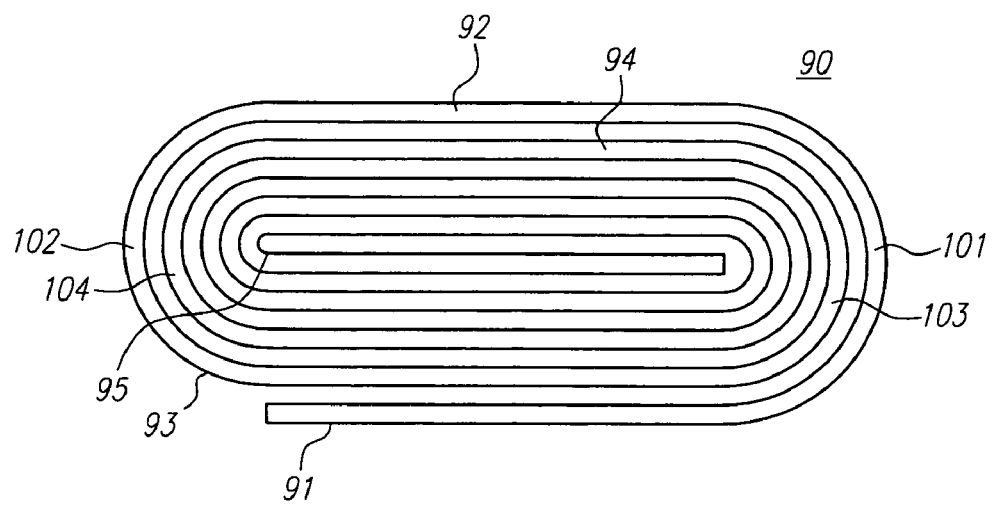
FIG. 6 is a plan view of a spiral snake resonator having no significant input and output pads.

FIG. 6 shows a plan view of a spiral snake resonator 90. A first long run 91 is connected to a second long run 92 by a first turn 101. The second long run 92 is connected to a third long run 93 which is disposed between the first long run 91 and the second long run 92, by a second turn 102. Second turn 102 has the same handedness as first turn 101. Third long run 93 is connected to a fourth long run 94 which is disposed between the second long run 92 and the third long run 93. The third turn 103 has the same handedness as the first turn 101 and second turn 102. This structure is repeated starting at a fourth turn 104 connected to the fourth long run 94 until terminating in a last long run 95 which is centrally disposed between the first long run 91 and second long run 92.

Figure 7:
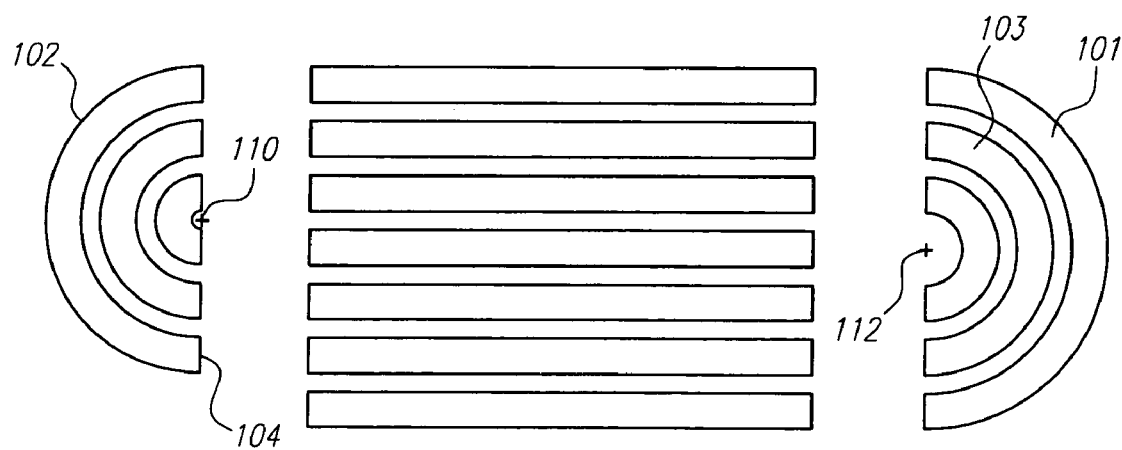
FIG. 7 is the spiral snake resonator of FIG. 6 with the end portions shown displaced from the linear portions of the structure.

FIG. 7 shows a spiral snake resonator with the turn portions (corresponding to 101, 102, 103 and 104 of FIG. 6) physically displaced from the long runs (91, 92 . . . 95 of FIG. 6) for clarity. In operation, these portions would be connected as shown in FIG. 6. FIG. 7 differs from FIG. 6 in that it includes seven long runs, as opposed to nine long runs for FIG. 6. Adopting the same number scheme as for FIG. 6, FIG. 7 shows that the even numbered turns 102, 104, dispose collectively at one end of the long runs, are concentric with each other around a point 110. Turns 101, 103 disposed on the right hand side of the long runs are concentric with each other around a point 112. The center of radius 112 is disposed on the end of the last long run 95. In contrast, the center of curvature 110 is disposed at the end of and between the last long run 95 and the preceding last long run. If there are N long runs, and the numbering convention is to sequentially number the long runs beginning with the outermost long run, the center point 110 is disposed between long runs N and N−1.

Figure 8:
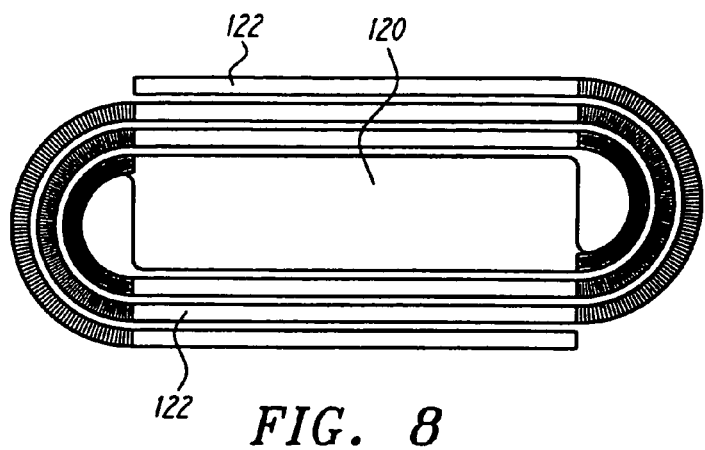
FIG. 8 is a plan view of a lumped, spiral in, spiral out resonator with a wide in the middle structure.

FIG. 8 shows a plan view of a spiral in, spiral out resonator having a wide portion in the middle region. The spiral in, spiral out aspects of FIG. 8 are as previously described in connection with FIG. 4. In contrast, FIG. 8 includes a center long run 120 (compared to the center long run 45 in FIG. 4) which is relatively wider than other long runs 122. The structure of FIG. 8 generally comprises a quasi-lumped element resonator structure particularly useful for bandpass and band reject filters. In the fundamental resonant mode, the peak circulating currents lie in the center of the resonator. Broadening the center conductor 120 increases the cross-sectional area of the transmission line, which allows for greater current transport. Generally, it is believed that this technique serves to alleviate the stress of large peak currents. The width of the center conductor 120 in FIG. 8 is six times as wide as the remaining conductor 122. However, resonators in which the width of the center long run 120 is at least twice as wide as the remaining long runs would utilize the concept of this invention.

Figure 9:
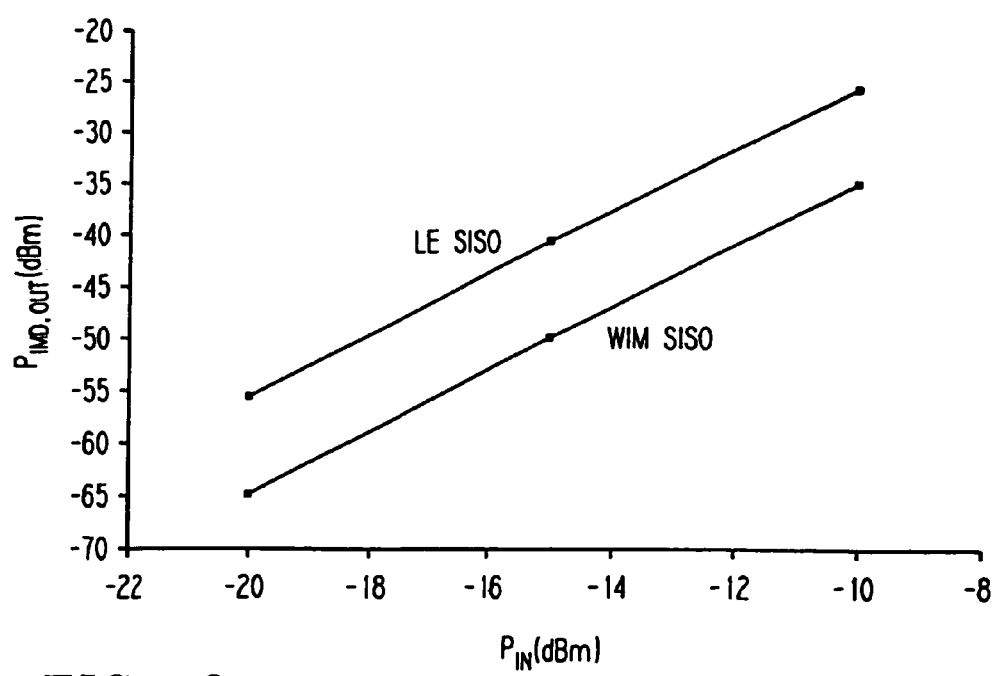
FIG. 9 is a graph of the intermodulation product as a function of input power for the lumped element spiral in, spiral out resonator and the wide in the middle spiral in, spiral out resonator.

FIG. 9 shows the intermodulation product ($P_{IMD,out}$) as a function of input power ($P_{in}$) for the structure of FIG. 5 (labeled LESISO for lumped element spiral in, spiral out) and the structure of FIG. 8 (labeled WIMSISO for wide in middle spiral in, spiral out). As can be seen, for a given power input, the wide in middle spiral in, spiral out resonator of the type shown in FIG. 8 has lower intermodulation compared to the lumped element spiral in, spiral out structure of FIG. 5.

Figure 10:
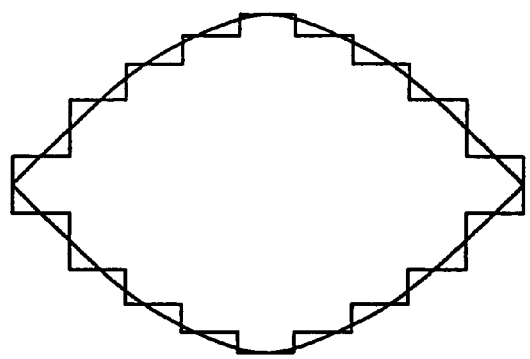
FIG. 10 is a emulation of a resonator utilizing an electromagnetic simulator.
Figure 11:
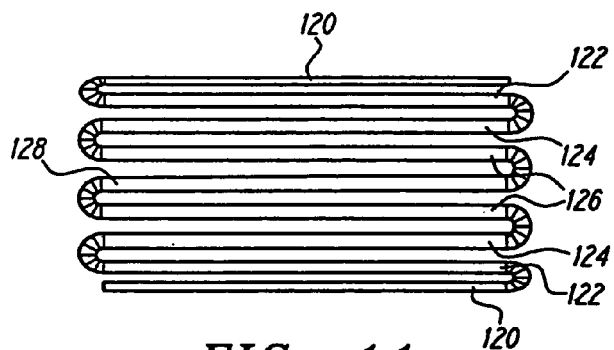
FIG. 11 is a zig-zag resonator having nonuniform thickness lined widths.

FIGS. 10, 11, 12 and 13 relate to graduated line width structures. FIG. 11 shows a zig-zag or serpentine resonator structure, but where the width of the conductors vary as a function of position within the resonator. External long runs 120 are relatively thinner than adjacent long runs 122, which are in turn thinner than next adjacent long runs 124, which are yet in turn relatively thinner than adjacent long runs 126. The center long run 128 is preferably larger than the remaining long runs.

Broadly, the technique disclosed herein is for increasing the line width of a folded HTS resonator as a function of current density. Considering a structure such as FIG. 3 with uniform width long runs 32 and uniform gaps between adjacent long runs, e.g., long run 32 and long run 34, if straightened out, would resemble a half wave resonator, assuming the fundamental mode. In this situation, the current distribution along the length of the resonator would be sin ($Q\pi x/\lambda$).

FIG. 10 shows a technique for simulating the resonator of the form shown in FIG. 11. If the resonator is considered to comprise long parallel runs, each having the same length, without consideration of the turns, the currents in the individual lines $I_i$ in terms of the maximum or minimum current ($I_{max}, I_{min}$) in a segment is as follows:

| i | $I_i/I_{max}$ | $I_i/I_{min}$ | Adjacent Leg Ratio |
|---|---|---|---|
| 1 | 0.158384338 | 1 | — |
| 2 | 0.459649276 | 2.902113197 | 2.902113197 |
| 3 | 0.715920617 | 4.520147809 | 1.557536699 |
| 4 | 0.902112776 | 5.695719602 | 1.26007375 |
| 5 | 1 | 6.31375561 | 1.108508854 |

-continued

| i | $I_i/I_{max}$ | $I_i/I_{min}$ | Adjacent Leg Ratio |
|---|---|---|---|
| 6 | 0.902112776 | 5.695719602 | 1.26007375 |
| 7 | 0.715920617 | 4.520147809 | 1.557536699 |
| 8 | 0.459649276 | 2.902113197 | 2.902113197 |
| 9 | 0.158384338 | 1 | — |

Figure 13:
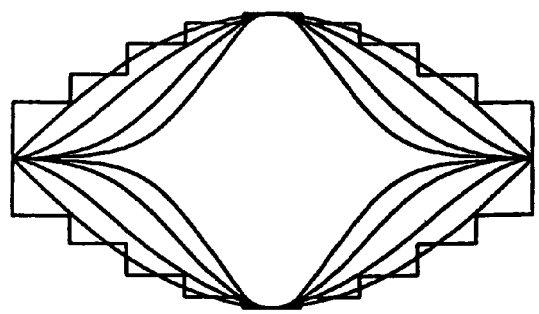
FIG. 13 is a output of an electromagnetic simulation.

Ideally, the structure of the graduated resonators would be smooth lines, such as shown in the smooth lines of FIG. 13. In certain applications (such as a linear, non-folded structure) it may be desirable to have the shape follow some power of the current distribution. However, when folding the resonators into the various disclosed shapes, e.g., spiral in, spiral out, zig-zag or snake, modified spiral, utilizing continuous change in the line width generally results in lines which are not parallel. By utilizing the generally parallel structures disclosed as the preferred embodiments herein, where the spacing between adjacent long runs may be made constant, modeling of such systems is made easier. However, devices utilizing the concepts of these inventions may be implemented where line widths vary continuously at some or all of the portions of the resonator.

Preferably, the ratio of widths from outside of long runs 120 at the ends of the resonator to adjacent segments is 1:3. However, under certain circumstances, this can create an impedance mismatch which becomes significant, and for practical size requirements utilizing current processing technology makes the width of the long runs too small or fine.

Figure 12:
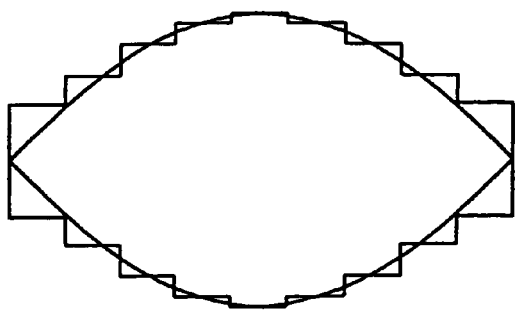
FIG. 12 is a depiction of the electromagnetic simulation.

FIG. 12 shows a modeling of a structure of FIG. 11 where the ratio between adjacent long runs 120, 122 is 2:3. Thus, to build a equivalent 9 long run zig-zag resonator with 0.3 millimeter lines and gaps, the total width is distributed over the lines as follows, numbers 6–9 mirroring 4–1:

| i | Ideal | Realization | Width (mm) | Gap (mm) |
|---|---|---|---|---|
| 1 | 1 | 2 | .146 | .1825 |
| 2 | 3 | 3 | .219 | .27375 |
| 3 | 4.5 | 4.5 | .3285 | .365 |
| 4 | 5.5 | 5.5 | .4015 | .41975 |
| 5 | 6 | 6 | .438 | |

Alternatively, the circuit may be modified in other ways. For example, if the circuit were split into three segments, as opposed to the nine segments described previously, the values would be approximately as follows:

| i | Ideal | Realization | Width (mm) | Gap (mm) |
|---|---|---|---|---|
| 1 | 1 | 1 | .243 | .243 |
| 2 | 1 | 1 | .243 | .243 |
| 3 | 1 | 1 | .243 | .3645 |
| 4 | 2 | 2 | .486 | .486 |
| 5 | 2 | 2 | .486 | |

FIG. 13 shows a modeling where the width of the long runs is varied as a function of a higher power of the current density. Under certain conditions, this arrangement may increase impedance mismatch at the ends of the resonator without any appreciable effect in the central region of the resonator where the currents are largest.

Figure 14:
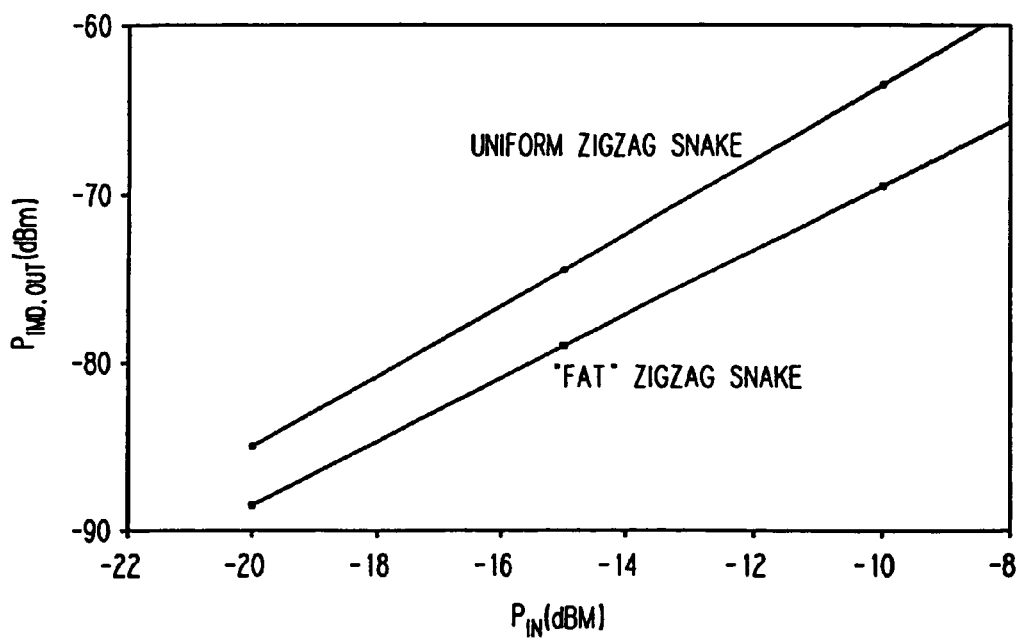
FIG. 14 is a plot of the intermodulation power output as a function of the power input comparing a uniform zig-zag snake resonator with a "fat" zig-zag snake.

FIG. 14 shows a graph of the intermodulation performance $P_{IMD, OUT}$ as a function of input power for a zig-zag or serpentine resonator as shown for example in FIG. 3 and a resonator having varying thickness long runs as shown for example in FIG. 11. The resonators have substantially equal resonator area, that is, they occupy substantially the same amount of overall area on a HTS film. FIG. 14 shows the structure of FIG. 11 (labeled "FAT" zig-zag snake) has a reduction of up to 5 dB in intermodulation product as compared to the structure of FIG. 3 (labeled uniform zig-zag snake).

Figure 15:
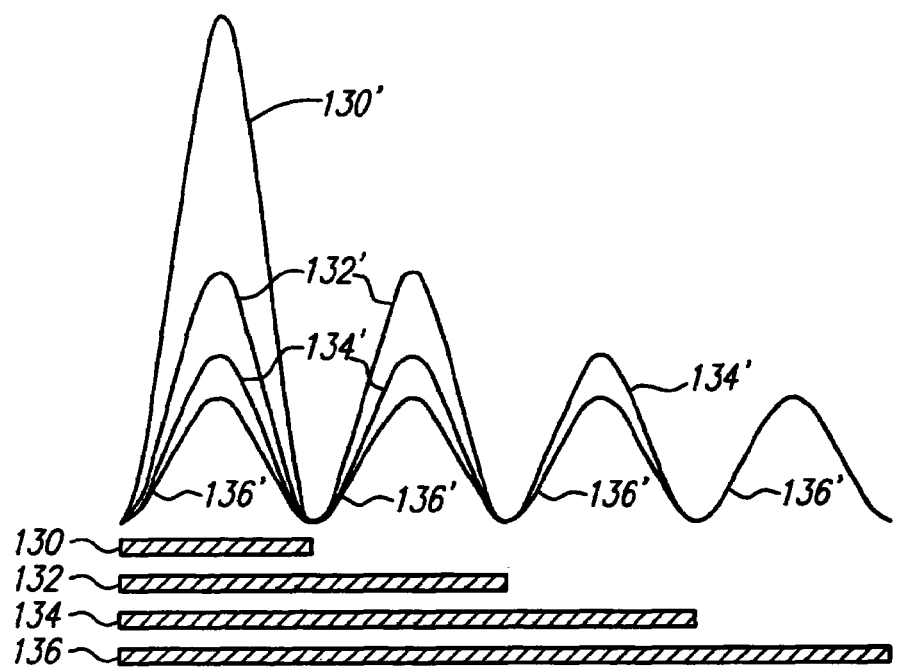
FIG. 15 shows resonate modes for an ideal straight resonator for fixed frequency and stored energy (loaded Q) showing the reduction in peak energy/current density when higher modes are employed.

FIG. 15 shows four resonators 130, 132, 134 and 136. Shown above those resonators is a graphic indicating the current as a function of position within the resonator. For ½ wavelength resonator 130, for a given resonant frequency and stored energy, the current distribution along the resonator is shown by line 130'. Similarly, clearly, for resonator 132, when in the next mode number (mode 1 where mode 0 is the lowest order mode) is shown by line 132'. Similarly, for resonator 134, when in the next mode number (mode 3), the current distribution along the resonator is shown by line 134'. Finally, for resonator 136, when in the next mode number (mode 4), the current distribution along the resonator is shown by line 136'. For a given resonant frequency and stored energy, the peak energy density is inversely proportional to the mode number. Utilizing higher modes serves to reduce the stress placed upon the resonator, and reduces intermodulation products. This discovery may be utilized in connection with any of the ½ wavelength resonators described herein.

Figure 16:
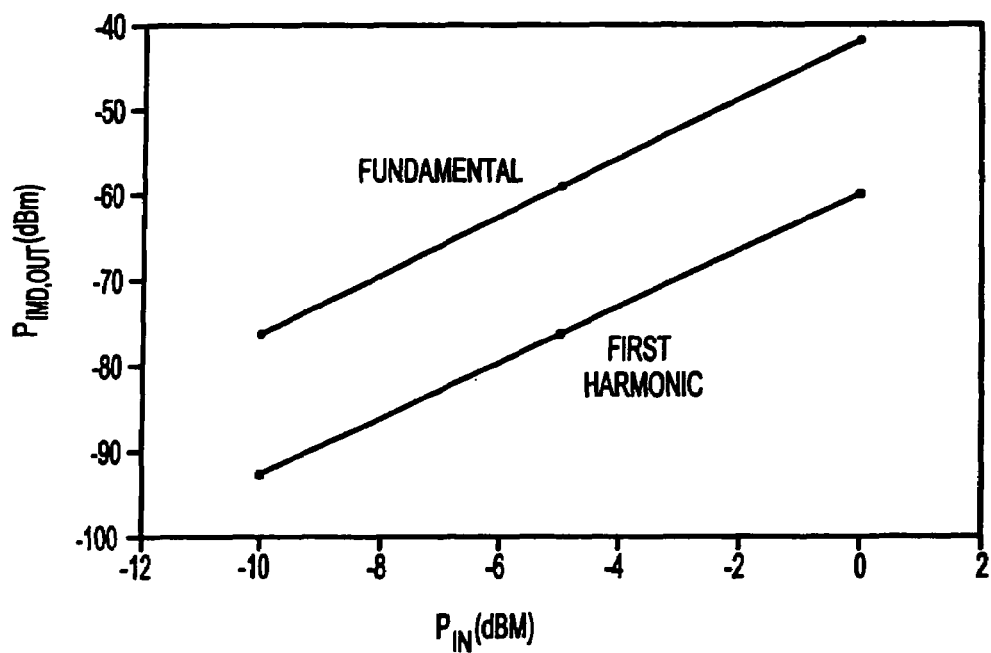
FIG. 16 shows a graph of the intermodulation product versus input power for the fundamental and first harmonic of a spiral in, spiral out resonator.

FIG. 16 shows a plot of the intermodulation product $P_{IMD, OUT}$ as a function of input power for the fundamental and first harmonic of a spiral in, spiral out resonator (See e.g., FIGS. 4 and 5). As can be seen, the first harmonic has lower intermodulation product as compared to the fundamental harmonic.

FIG. 17b shows a zig-zag or snake resonator operable at a first harmonic, where FIG. 3 in comparison would show a zig-zag or snake resonator at the fundamental frequency. If it is desired to preserve the circuit area, but to use the first harmonic as in FIG. 17b as compared to the fundamental in FIG. 3, the width of the long runs is reduced, preferably halved, in order to double the electrical length of the resonator. FIG. 17b shows a resonator operable at a first harmonic and utilizing the wide at peak structure described in conjunction with FIGS. 15 and 16, above. Thus, the structure of 17b when operated at the first harmonic has two regions corresponding to the relatively wider regions of the long runs at which the current density is reduced. This wide at peaks resonator structure advantageously improves the intermodulation performance. The principals of the wide at peaks technique may also be applied to spiral in, spiral out snake resonators. In such resonators, due to the nature of the spiral in, spiral out folding, the odd harmonics of the resonator are closer to that of a spiral resonator in its fundamental mode.

FIGS. 18a and 18b show the magnitude and phase, respectively, on a modeled system of a spiral in, spiral out resonator. The modeled structure is based upon a resonator of the structure shown in FIG. 4 and described above. As shown, the system is modeled as having 'single turns' which are linear and substantially parallel to adjacent 'turns'. While this structure is advantageously utilized for modeling, it may also be utilized in physical implementations of the structures. Indeed, the structures described herein may be utilized with round or rounded turns, squared turns, mitred turns, or any turn serving as an interconnection between the long runs which does not materially negatively impact the achieving the goals or objects of these inventions. One source for modeling software is Sonnet Software, Incs., Suite of Planar 3DEM Tools (referred to either as "Sonnet" or "em") and is available from Sonnet Software, Inc., 10207 North Street, Suite 210, Liverpool, N.Y. 13088. The magnitude shown in FIG. 18a increases from the ends of the resonators to a maximum value in the middle of the center line. The frequency of modeling is 0.71742 GHz. The phase shows that segments in the odd numbered long runs (40, 43, 45, 47, and 49 in FIG. 4 and also in FIGS. 18B and 18D) have a phase substantially 180° opposite to that of the even numbered long runs (40, 42, 44, 46 and 48 in FIG. 4 and also in FIGS. 18B and 18D).

FIGS. 18c and 18d show the magnitude and phase respectively for the simulation of the same spiral in, spiral out resonator but at the first harmonic. The magnitude shows that the magnitude rises from the ends of the resonator to two peaks situation roughly at ¼ and ¾ of the length of the line, with the magnitude decreasing from the peaks to the center of the resonator. The phase shown in FIG. 18d shows that the resonator in substantially the upper half is of one phase, whereas the resonator in substantially the bottom half is of 180° phase difference. The phase change is at substantially the center of the middle long run (long run 45 in FIG. 4).

It has been discovered that the use of a symmetric mode, that is, one in which currents flow in the same direction in adjacent legs of the resonator, such as is shown in FIG. 18b, provide superior results. Specifically, the use of the symmetric mode serves to reduce current densities relative to the asymmetric mode. One of the direct beneficial results of reduction in current density is the reduction in intermodulation effects. While the asymmetric mode, that is, one in which currents flow in opposite directions in adjacent legs of the resonator, are beneficial respecting far field shielding, if the far field effects can be pushed sufficiently away the symmetric mode has the benefit described previously.

Experimental Results

The following table provides data regarding spiral resonators, and spiral in, spiral out snake resonators of the size and area identified.

most long runs correspond to values 141, 149, the adjacent long runs corresponding to values 142, 148, 143, 147, 144 and 146 to the value 145 of the center resonator. As can be seen, the current is opposite directions for adjacent lines (compare the positive value of 141 with the negative value of 142). In the higher mode spiral in, spiral out resonator (FIGS. 18b and 18d and lower right graph in FIG. 19d labeled ALF SISO), again utilizing the same number convention, shows that adjacent resonators corresponding to values 151, 152, 153 and 154 are all negative, indicating current flow in the same direction. In contrast, current in long runs corresponding to values 156, 157, 158 and 159 run in the same direction, that direction being opposite to the direction of current in the long runs corresponding to values 151, 152, 153 and 154. As shown, the value 155 corresponding to the center resonator is shown substantially at 0. As can be seen in the graphics of FIG. 19d, the current shows divergences at the edges of the long runs of the resonator. Further, while the ALF SISO of FIG. 19d is at a higher frequency (then a harmonic) as compared to the fundamental frequency such as used in the SISO of FIG. 19c, the ALF SISO shows a lower envelope, corresponding to lower current density as compared to the other structures shown.

Figure 20:
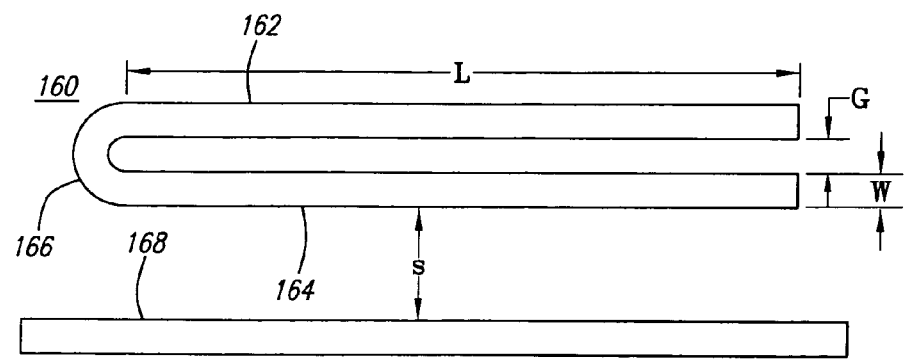
FIG. 20 shows a plan view of a hairpin resonator.

FIG. 20 shows a plan view of a hairpin resonator 160. The hairpin resonator 160 is characterized in having a first long run 162 having a length L and a width W, and a second long run 164, also having a length L and width W, the first long run 162 and second long run 164 being substantially parallel to each other, and separated by a gap G. The long runs 162, 164 are connected to turn 166. The hairpin resonator 160 is spaced a distance S from conductor 168, and is generally parallel to the long runs 162, 164. It has been discovered that the particularly geometry affects both the losses and intermodulation in these resonators. The first harmonic mode gives less intermodulation relative to the fundamental mode, though the first harmonic mode has relatively higher losses relative to the fundamental mode, believed to be due to the more extended fields of that mode. In operation, microwave energy may be coupled to these resonators in a band reject

| Topology | Spiral | Spiral | SISO Snake | SISO Snake | SISO Snake | SISO Snake |
|---|---|---|---|---|---|---|
| Length [mm] | 10.41 | 10.41 | 8.8175 | 8.8175 | 16.25 | 16.37 |
| Width [mm] | 4 | 4 | 6.4 | 6.4 | 3.6009 | 7.0025 |
| Area [cm$^2$] | 0.4164 | 0.4164 | 0.56432 | 0.56432 | 0.58514625 | 1.14630925 |
| LineWidth [mm] | 0.4 | 0.4 | 0.4 | 0.4 | 0.4 | 1 |
| Gap [mm] | 0.2 | 0.2 | 0.2 | 0.2 | 0.4 | 0.5 |
| Frequency [MHZ] | 829.285 | 829.5 | 849.291 | 849.19 | 865.866 | 869.206 |
| Unloaded Q | 39800 | 37700 | 27200 | 37000 | 53500 | 65300 |
| Loaded Q | 4130 | 4000 | 4130 | 4610 | 3570 | 3440 |
| IMD @-20 dBm[dBc] | −55.5 | −76 | −62.5 | −58.5 | −66 | −69 |
| IMD @-20 dBm [dBc] (QL~1000) | −80.1 | −100.1 | −87.1 | −85.0 | −88.1 | −90.5 |

Figure 19A:
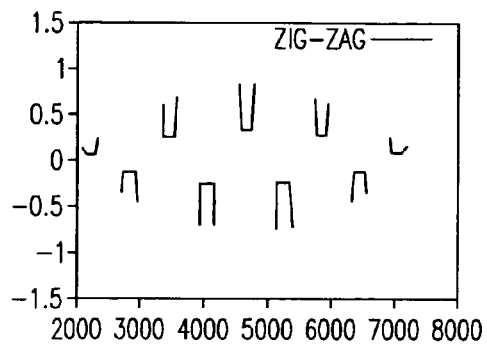
FIGS. 19a, 19b, 19c and 19d show current density cross sections for a zig-zag, spiral in, spiral out, spiral and ALF spiral in, spiral out resonators using a planar 3D electromagnetic simulations package developed by US company Sonnet, Inc.
Figure 19B:
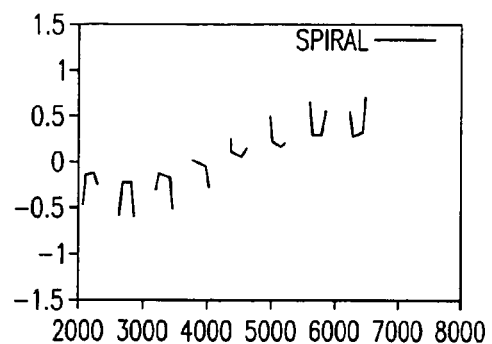
Figure 19C:
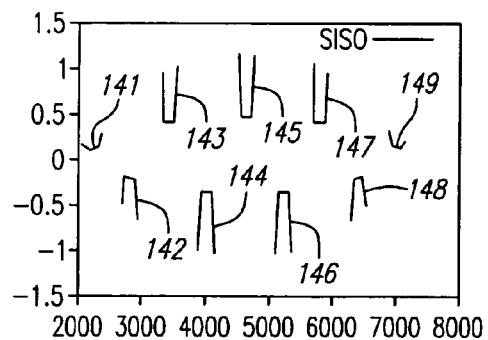
Figure 19D:
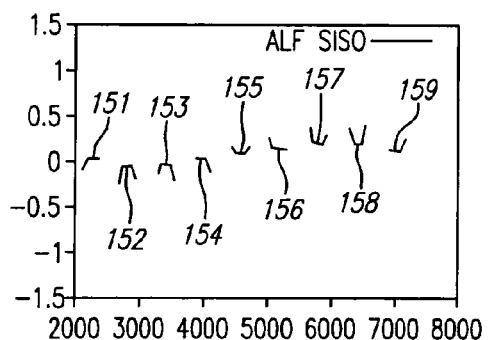

FIGS. 19a, 19b, 19c, 19d show Sonnet current density cross-sections for zig-zag, spiral in, spiral out, spiral and higher mode (ALF) spiral in, spiral out resonators. Specifically, FIGS. 19c and 19d show quantitative results for a resonator cut line in a vertical direction such as labeled on cut 19 in FIG. 18a and FIG. 18b. Thus, for the spiral in, spiral out structure in the fundamental mode (FIGS. 18a and 18c and lower left figure in FIG. 19c labeled SISO) the current density can be seen to alternate in direction from adjacent long runs. Thus, in FIG. 19c SISO, the external fashion via the transmission line 168. The spacing S between the transmission line 168 and the resonator 160 determines the strength of the coupling and thus the energy stored in the resonator, which may be characterized in terms of the loaded quality factor $Q_L$ of the device.

The response of the band reject resonator may be characterized in terms of three quantities, the resonance frequency, $F_0$, and the loaded and unloaded quality factors, $Q_L$ and $Q_U$, respectively. $F_0$ and $Q_L$ are determined by the geometry of the resonator 160 and substrate.

For the actual experiments performed, the width of the runs 162, 164 was fixed at 0.4 mm, with L, G and S being adjustable parameters. The resonance frequency of 7.4 GHz was chosen.

Figure 21A:
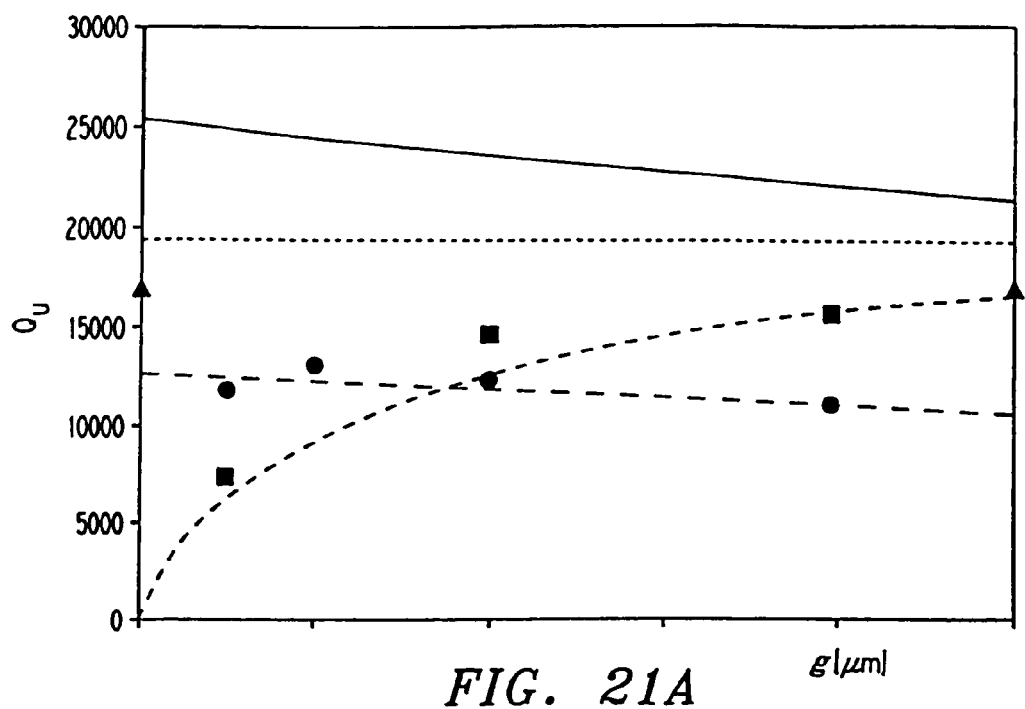
FIG. 21a shows a graph of the unloaded Q ($Q_U$) as a function of gap width.

FIG. 21a shows a graph of the unloaded quality factor ($Q_u$) of the gap g for a series of hairpin resonators. The experimental results for the symmetric resonators (second mode, represented by circles), the antisymmetric resonators (first mode, represented by squares) and the straight resonator (represented by triangles) are compared with numerical calculations (solid, long-dashed, and short-dashed line, respectively). The dotted line accounts for the losses in the lid for the symmetric resonators.

Figure 21B:
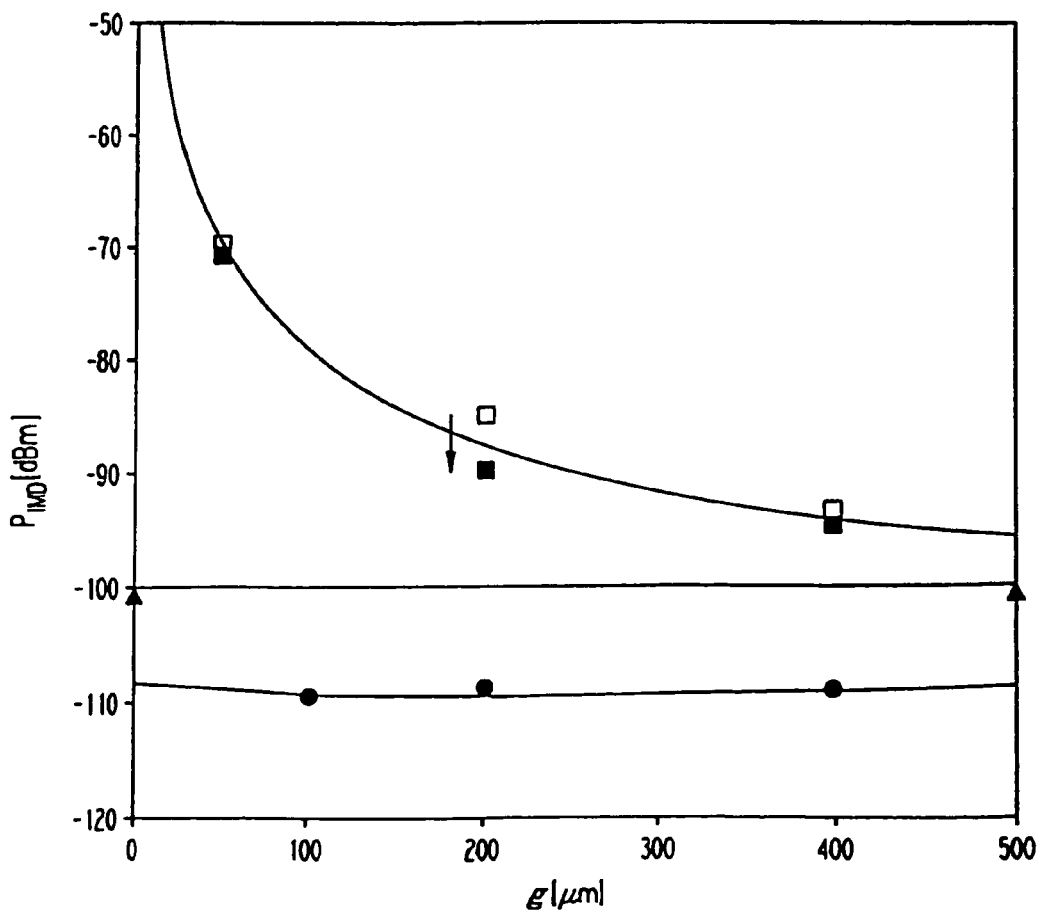
FIG. 21b shows a graph of the intermodulation power $P_{IMD}$ as a function of gap width.

FIG. 21b shows a graph of the intermodulation power $P_{IMD}$ measured in decibels as a function of gap g for a series of hairpin resonators. The experimental results for the symmetric resonators (second mode, represented by circles), the antisymmetric resonators (first mode, represented by squares) and the straight resonator (represented by triangles) are compared with numerical calculations (solid, long-dashed, and short-dashed line, respectively). The open symbols represent the raw data as measured before correction to $\tilde{Q}=1700$. The intermodulation power is measured in decibels referenced to 1 mW.

Figure 22:
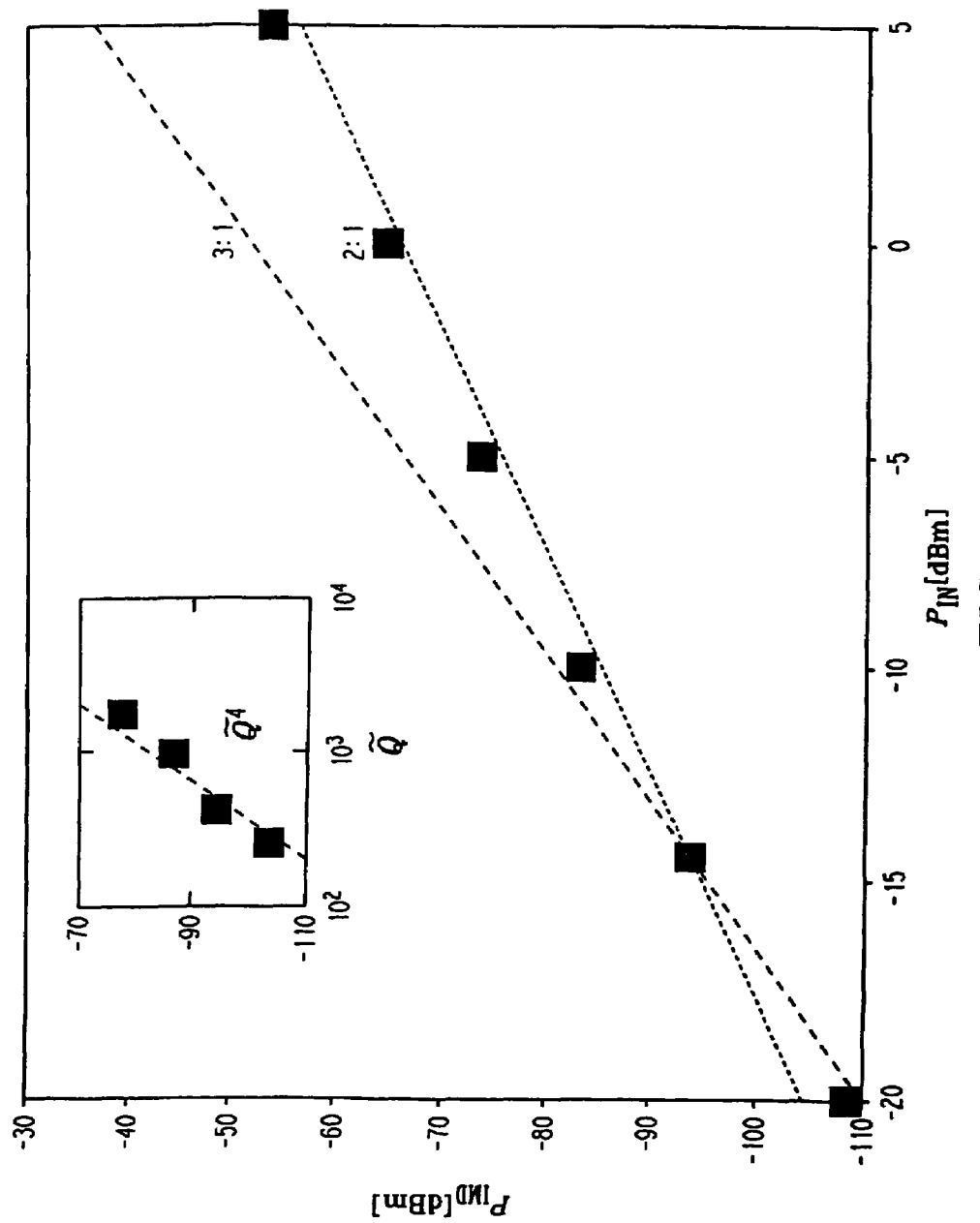
FIG. 22 shows a graph of the intermodulation power $P_{IMD}$ as a function of input power $P_{IN}$ for a hairpin resonator.

FIG. 22 shows a graph of the intermodulation power $P_{IMD}$ for a hairpin resonator as a function of the input power $P_{IN}$ of the fundamental signals. Both powers are measured in decibels referenced to 1 mW. Inset: $P_{IMD}$ as a function of $\tilde{Q}=Q_L(1-Q_L/Q_U)$. The data are consistent with the theoretical expected $P_{IMD} \propto \tilde{Q}^4$.

Figure 23A:
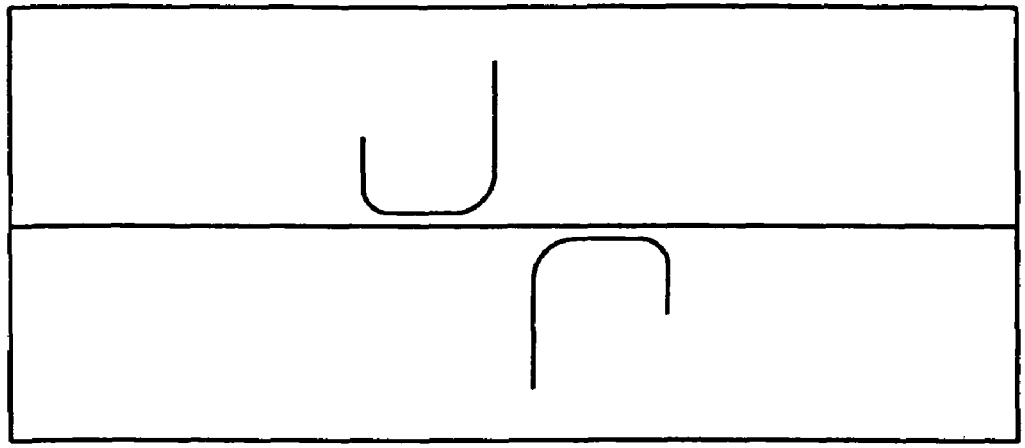
FIGS. 23a and 23b show graphs of the current in the hairpin resonator of FIG. 20 in the fundamental mode (FIG. 23a) and the harmonic mode (FIG. 23b).
Figure 23B:
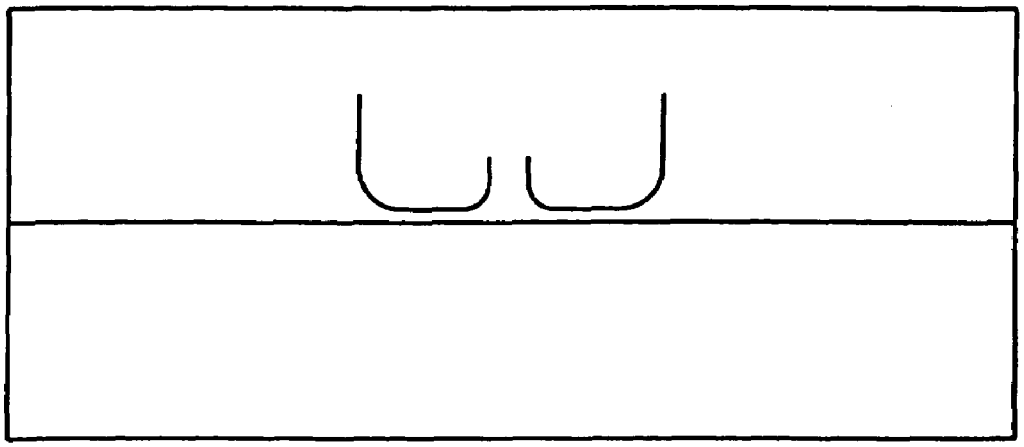

FIG. 23a shows a graph of the current in the hairpin resonator of FIG. 20 in the fundamental mode. The current can be seen to flow in opposite directions in adjacent legs of the hairpin resonator 160. FIG. 23b shows the current distribution in the hairpin resonator 160 in the harmonic mode. The current can be seen to run in the same direction in adjacent long runs 162, 164, thus operating in the symmetric mode.

Four sets of resonators were designed:

1. For gap widths of g=0.4, 0.2, 0.1 and 0.05 mm, L (long run length) and S (spacing from conductor) were adjusted so that the first resonance was at $f_0$=7.4 GHz with $Q_L$=2000, resulting in L~4 mm and S~1 mm. As the microwave currents flow in opposite directions in the two legs of the resonator these will also be referred to as anti-symmetric resonators.
2. For gap widths of g=0.4, 0.2, 0.1 and 0.05 mm, L and S were adjusted so that the second resonance was at $f_0$=7.4 GHz with $Q_L$=2000, resulting in L~7 mm and S~2 mm. Since the currents flow in the same direction in the two legs of the resonator these will be referred to as symmetric resonators.
3. For a gap width of g=0.4 mm, L and S were adjusted so that the second resonance remained at $f_0$=7.4 GHz but the coupling strength varied at $Q_L$=2000, 1000, 500, 200.
4. A straight resonator was designed so that its first resonance was at $f_0$=7.4 GHz with $Q_L$=2000, resulting in L~7.7 mm and S~2 mm.

The circuits were clipped into gold plated test fixtures using Indium foil below the circuit to ensure proper thermal and electrical contact. The microwave circuit was then completed by wire bonds at both ends of the 50 Ω thru line. Note that the electrical ground plane seen by the resonator is, for the most part, provided by the unpatterned film on the back side of the substrate.

The microwave transmission characteristics, S21, were measured using HP 8720B Vector Network Analyzer in order to determine $f_0$, $Q_U$ and $Q_L$ which characterize the linear response of the circuit at low microwave powers. The Qs are obtained from direct measurements of the fractional bandwidths at −3 dB, $\Delta f_{-2\ dB}$, the insertion loss, $S_{21}(f_0)$, and the width of the resonance 3 dB above the minimum, $\Delta f_{+3\ dB}$. In all cases the input power to the resonators was held fixed in $P_{IN}$=−20 dBm.

The measured and calculated Qs are presented in FIG. 21A. In the calculations a surface resistance of $R_s$=210 μΩ at 7.4 GHz and a penetration depth of $\lambda(77K)$=0.3 μm were used.

For the antisymmetric resonators the calculations are in good agreement with the measurements. For smaller gap sizes $Q_U$ is degraded. This can be understood from the antiparallel currents running in the gap region. Therefore, high current densities have to flow at the inner edges of the legs to screen out this field from the superconducting films. These high current densities lead to increased losses and to higher intermodulations. In contrast, for the symmetric mode the parallel currents lead to fields that cancel within the gap and no such degradation is expected. For this mode we find almost exactly double what is measured (the dotted line shows half of the calculated values), using the same surface impedances used to evaluate the anti-symmetric mode Qs.

The circuits were tested with and without an Aluminum lid placed 0.150 inches above the circuit. For the first set of resonators the effect of removing the lid was only a slight shift in the resonant frequency with no detectable change in $Q_U$ or $Q_L$. For the resonators which made use of the first harmonic (sets 2 and 3), the effect was far more severe; there $Q_U$ dropped close to an order of magnitude as the lid was removed. This is an indication that the microwave fields associated with the resonator are far more extended for the symmetric modes than for the anti-symmetric ones.

The two microwave signals required to produce intermodulation products were symmetrically placed 15 kHz above and below $f_0$, for a signal separation of 30 kHz. Continuous Wave (CW) Signals were produced using HP 8341B and HP 83640A synthesized sweepers, and the signals detected using a Tektronix 3784 Spectrum Analyzer. The output power of the two sources was measured using an HP 437B power meter, and adjusted so that the two signals arrived at the sample with the same magnitude.

The absolute magnitude of third order intermodulation products. $P_{IMD}$, as a function of input power provided to the device, $P_{IN}$ was measured. For the 30 kHz signal separation we are using here these signals are generated at $f_0$±45 kHz. As can be seen in FIG. 22, $P_{IMD}$ has a slope much closer to 2:1 (dotted line) than the 3:1 (dashed line) expected from a pure third order nonlinearity.

$P_{IMD}$ at a fixed input power of $P_{IN}$=−20 dBm is presented as a function of gap width for the first two sets of resonators and the straight one in FIG. 21b. $P_{IMD}$ was set to Q=1700 using the intermodulation value as proportional to the fourth power of Q. The open symbols denote the raw data while the full ones denote the adjusted values.

Figure 24:
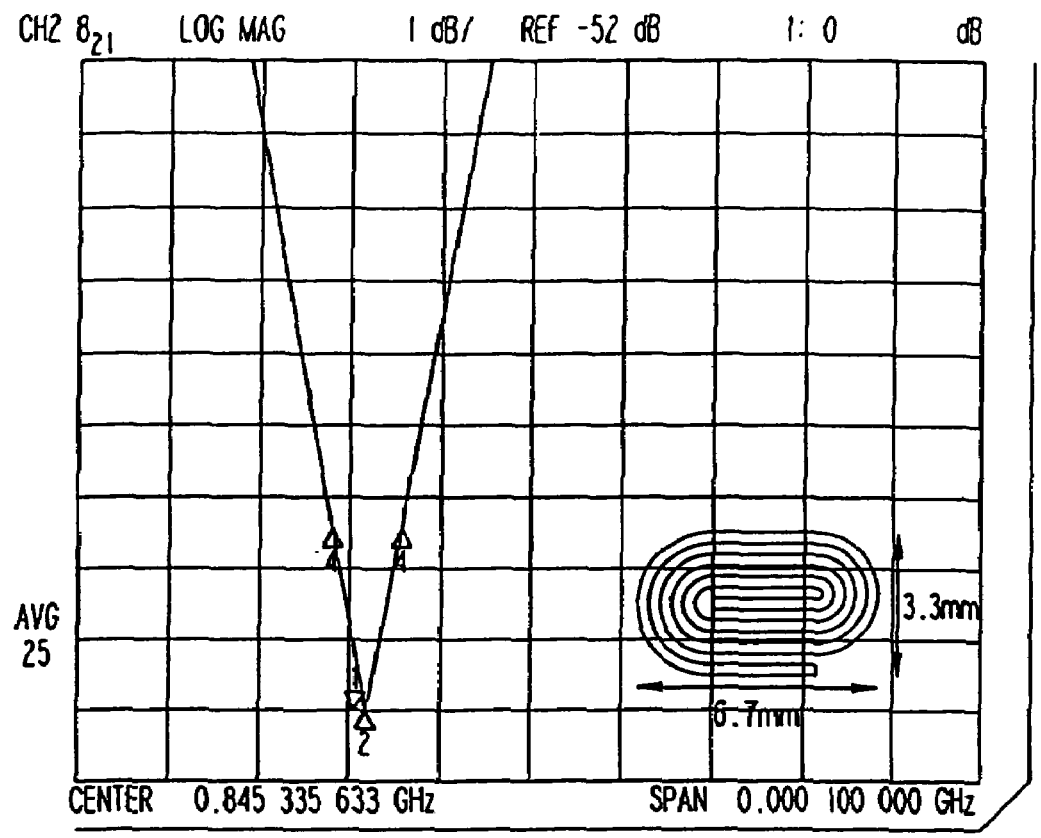
FIG. 24 shows results of operation of a resonator of this invention.

FIG. 24 shows the frequency response of the S-parameter for the fundamental resonance of a spiral snake resonator shown in an inset. The substrate thickness was 0.020". The dimensions of the resonance thus realized are 3.3 mm by 6.7 mm, which is shown in the inset. The measured unloaded quality factor was 101450 at 845.318 MHz at a temperature of 77K.

Figure 25A:
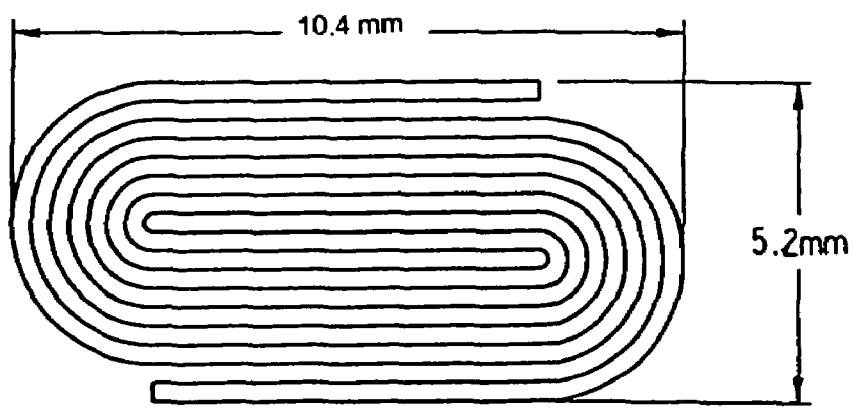
FIG. 25a illustrates a spiral in, spiral out resonator according to one embodiment of the invention.

FIG. 25a shows a spiral in, spiral out snake resonator. When realized with YBCO films deposited on 0.015" thick MgO substrates the resonator was 5.2 mm by 10.4 mm in area. The average unloaded quality factor of these resonators was measured to be 110,000 at a resonance frequency 845 MHz and a temperature of 77K.

Figure 25B:
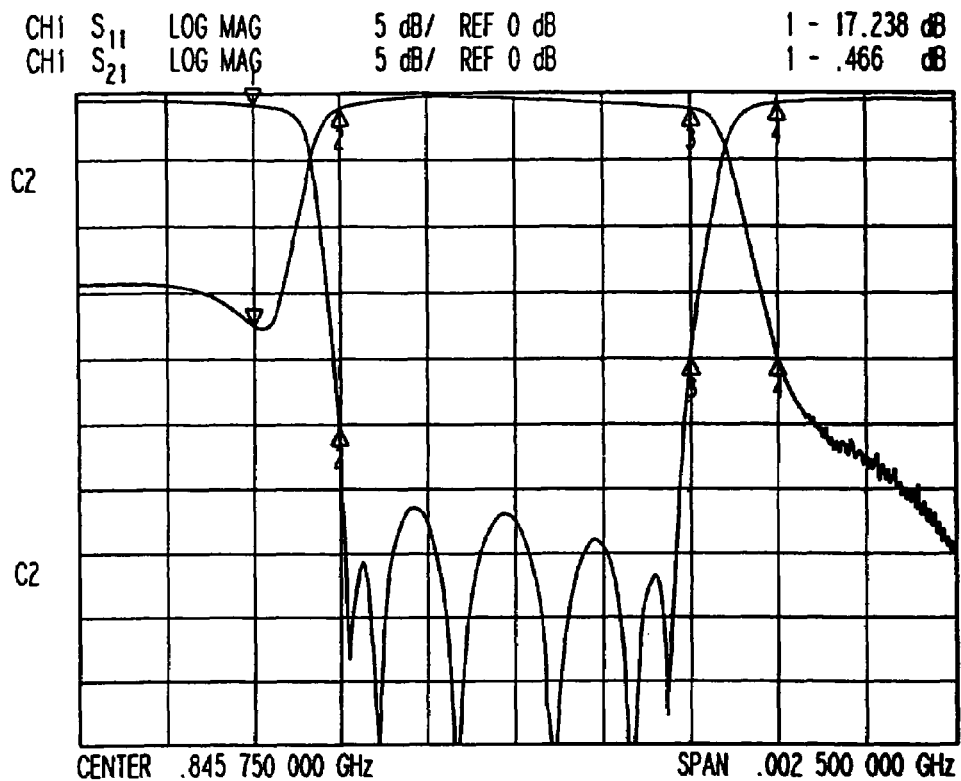
FIGS. 25b and 25c show results of operation of a resonator of this invention.

FIG. 25b shows the measured frequency response of the S-parameters for a quasi elliptic band reject filter realized using six of the resonators in FIG. 25a.

Figure 25C:
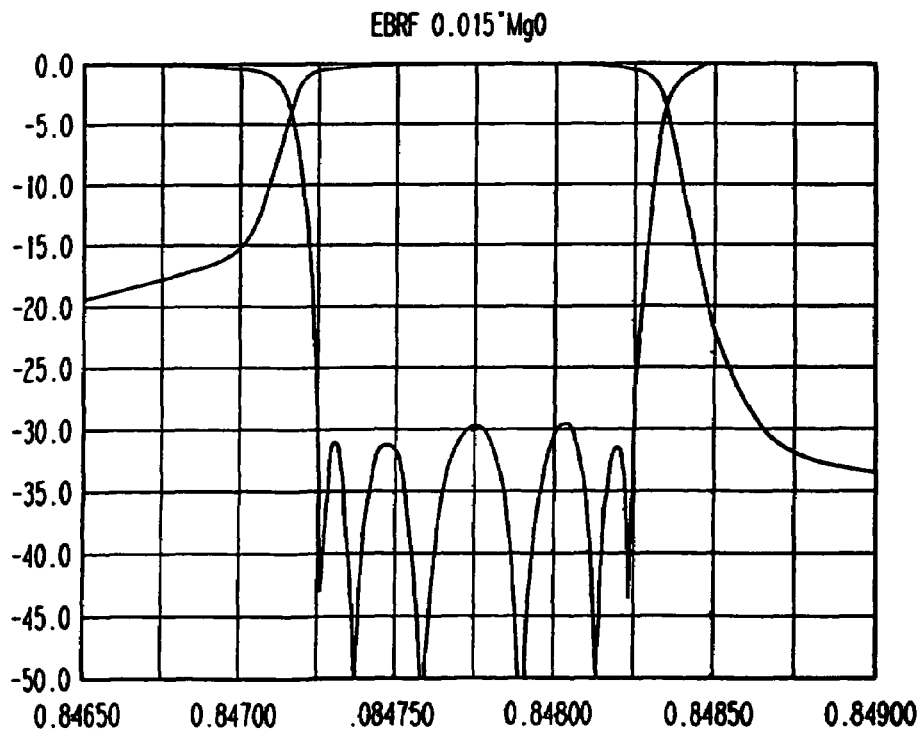

FIG. 25c shows a simulation of the filter in 25b taking the average measured unloaded quality factor into account. The unloaded quality factor is apparent in the depth of the nulls as well as the sharpness in the corners of the filter.

Figure 26:
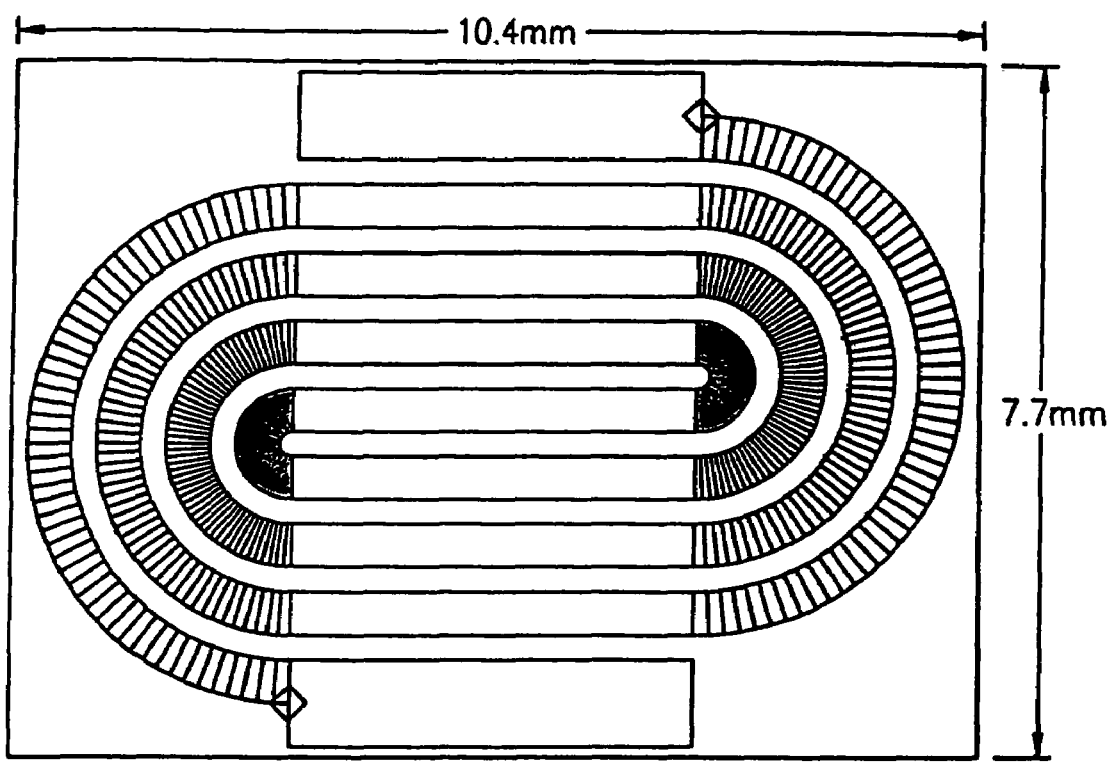
FIG. 26 illustrates a spiral in, spiral out resonator according to one embodiment of the invention.

FIG. 26 shows an spiral-in-spiral-out resonator with moderately enlarged capacitor pads. When realized using TBCCO films deposited on 0.020" LaAlO$_3$ the resonator is 7.7 mm by 10.4 mm in area. When operated in the "ALF" mode, the resonant frequency of this resonator is 846.477 MHz, and the resonator had a measured unloaded quality factor of 150,050 at a temperature of 77K.

Figure 27:
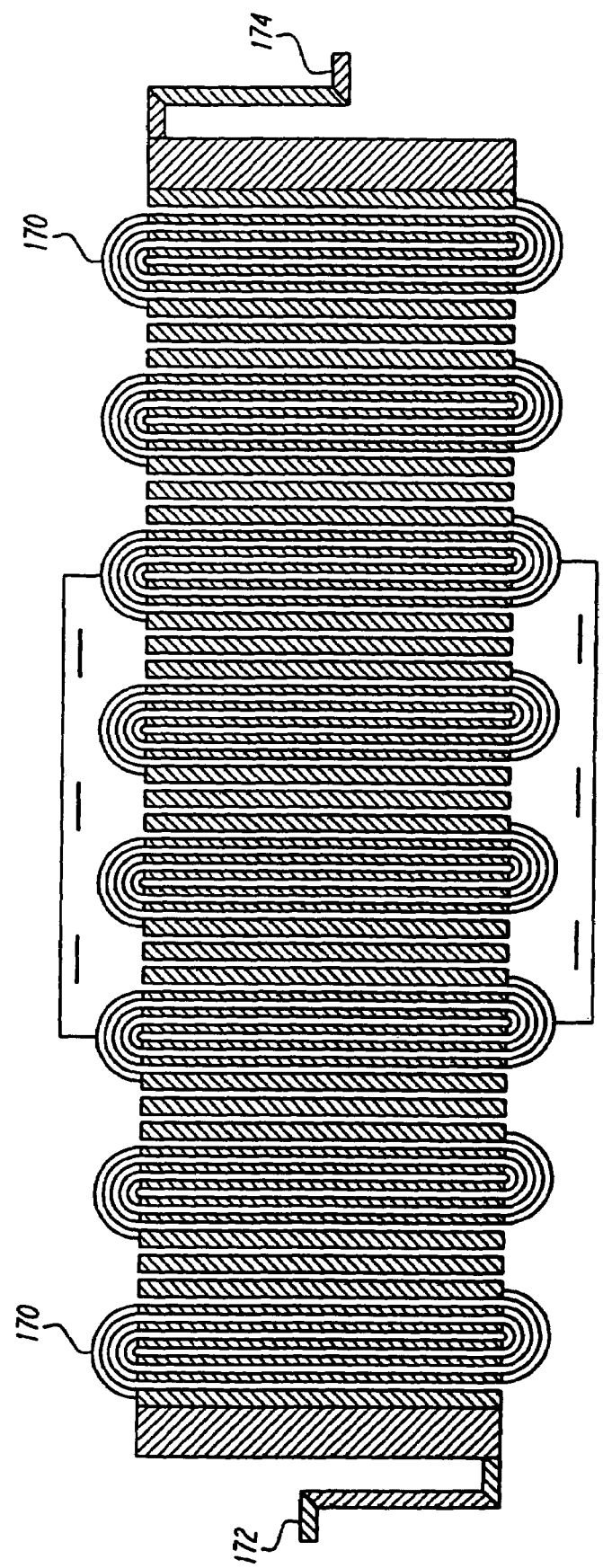
FIG. 27 shows a plan view of a filter utilizing a spiral in, spiral out structures.

FIG. 27 shows a plan view of a filter structure having a plurality of spiral in, spiral out structures 170, with side coupling therebetween. An input 172 and an output 174 provide signal coupling to the filter structure.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A snake resonator, comprising:
   a plurality of N long runs, each one of the plurality of N long runs having two ends; and
   a plurality of turns connecting the plurality of N long runs to each other in a spiral snake configuration, characterized in that one end of a first long run of the plurality of N long runs is connected to one end of a second long run of the plurality of N long runs by a first turn of the plurality of turns, the other end of the second long run is connected to one end of a third long run of the plurality of N long runs by a second turn of the plurality of turns, the remaining long runs of the plurality of N long runs being by repeating the connections of the first, second and third long run for the remaining plurality of N long runs using the remaining plurality of turns starting at the other end of the third long run and terminating at one end of the Nth long run of the plurality of N long runs;
   wherein certain ones of the long runs are wider than certain other ones of the long runs, the wider runs being those that would have a higher current density if all runs were of equal width.

2. The snake resonator of claim 1 wherein there are three long runs.

3. The snake resonator of claim 1 wherein there are four long runs.

4. The snake resonator of claim 1 wherein N is 5.

5. The snake resonator of claim 1 wherein N is 7.

6. The snake resonator of claim 1 wherein N is 9.

7. The snake resonator of claim 1 wherein N≧9.

8. The snake resonator of claim 1 wherein the plurality of N long runs are substantially parallel to each other and the spacing between adjacent long runs of the plurality of N long runs is substantially constant.

9. The snake resonator of claim 8 wherein a ratio of the width between at least two adjacent long runs of the plurality of N long runs is approximately 2:3.

10. The snake resonator of claim 1 wherein the plurality of N long runs are substantially parallel to each other and a ratio of the width between at least two adjacent long runs of the plurality of N long runs is approximately 2:3.

11. The snake resonator of claim 1 wherein the snake resonator has a fundamental resonant frequency and the snake resonator defines an electrical length substantially equal to ½ the wavelength of the fundamental resonant frequency.

12. The snake resonator of claim 1 wherein the resonator has a Q of at least 1,000.

13. The snake resonator of claim 1 wherein the resonator has a Q of at least 10,000.

14. The snake resonator of claim 1 wherein the resonator has a Q of at least 50,000.

15. The snake resonator of claim 1, wherein the plurality of N long runs and the plurality of turns are comprised of a high temperature super conducting material.

16. The snake resonator of claim 15 wherein the high temperature superconducting material is a thallium containing superconductor.

17. The snake resonator of claim 15 wherein the high temperature superconducting material is a YBCO high temperature superconductor.

18. The snake resonator of claim 1 wherein the plurality of N long runs and turns are formed in a thin film disposed on a substrate.

19. The snake resonator of claim 18 wherein a ground plane is disposed on the substrate.

20. The snake resonator of claim 1 wherein the snake resonator is a spiral-in, spiral-out resonator.

21. A snake resonator, comprising:
   a plurality of N long runs, each one of the plurality of N long runs having two ends; and
   a plurality of turns connecting the plurality of N long runs to each other in a snake configuration, characterized in that one end of a first long run of the plurality of N long runs is connected to one end of a second long run of the plurality of N long runs by a first turn of the plurality of turns, the other end of the second long run is connected to one end of a third long run of the plurality of N long runs by a second turn of the plurality of turns, the remaining long runs of the plurality of N long runs being by repeating the connections of the first, second and third long run for the remaining plurality of N long runs using the remaining plurality of turns starting at the other end of the third long run and terminating at one end of the Nth long run of the plurality of N long runs, wherein the plurality of N long runs are substantially parallel to each other and a ratio of the width between at least two adjacent long runs of the plurality of N long runs is approximately 2:3;
   wherein certain ones of the long runs are wider than certain other ones of the long runs, the wider runs being those that would have a higher current density if all runs were of equal width.

22. The snake resonator of claim 21 wherein the snake resonator is a spiral-in, spiral-out resonator.

23. The snake resonator of claim 21 wherein the snake resonator is a zig-zag resonator.

24. The snake resonator of claim 21 wherein there are three long runs.

25. The snake resonator of claim 21 wherein there are four long runs.

26. The snake resonator of claim 21 wherein N is 5.

27. The snake resonator of claim 21 wherein N is 7.

28. The snake resonator of claim 21 wherein N is 9.

29. The snake resonator of claim 21 wherein $N \geq 9$.

30. The snake resonator of claim 21 wherein the spacing between adjacent long runs of the plurality of N long runs is substantially constant.

31. The snake resonator of claim 21 wherein the snake resonator has a fundamental resonant frequency and the snake resonator defines an electrical length substantially equal to ½ the wavelength of the fundamental resonant frequency.

32. The snake resonator of claim 21 wherein the resonator has a Q of at least 1,000.

33. The snake resonator of claim 21 wherein the resonator has a Q of at least 10,000.

34. The snake resonator of claim 21 wherein the resonator has a Q of at least 50,000.

35. The snake resonator of claim 21, wherein the plurality of N long runs and the plurality of turns are comprised of a high temperature super conducting material.

36. The snake resonator of claim 35 wherein the high temperature superconducting material is a thallium containing superconductor.

37. The snake resonator of claim 35 wherein the high temperature superconducting material is a YBCO high temperature superconductor.

38. The snake resonator of claim 21 wherein the plurality of N long runs and turns are formed in a thin film disposed on a substrate.

39. The snake resonator of claim 38 wherein a ground plane is disposed on the substrate.

40. The snake resonator of claim 21 wherein the snake resonator is a spiral resonator.

* * * * *